(12) United States Patent
Chen et al.

(10) Patent No.: US 6,461,618 B1
(45) Date of Patent: Oct. 8, 2002

(54) **74 KILODALTON OUTER MEMBRANE PROTEIN FROM *MORAXELLA CATARRHALIS***

(75) Inventors: Dexiang Chen, Madison, WI (US); Karl R. VanDerMeid, Rochester, NY (US); John C. McMichael, Rochester, NY (US); Vicki L. Barniak, Rochester, NY (US)

(73) Assignee: American Cyanamid Company, Madison, NJ (US)

(*) Notice: Subject to any disclaimer, the term of this patent is extended or adjusted under 35 U.S.C. 154(b) by 0 days.

(21) Appl. No.: 09/355,398

(22) PCT Filed: Jan. 29, 1998

(86) PCT No.: PCT/US98/01840

§ 371 (c)(1), (2), (4) Date: Oct. 21, 1999

(87) PCT Pub. No.: WO98/33814

PCT Pub. Date: Aug. 6, 1998

Related U.S. Application Data

(60) Provisional application No. 60/036,827, filed on Jan. 31, 1997.

(51) Int. Cl.[7] .................. A61K 39/02; A61K 39/00; C07H 21/04; C12P 21/06; C12N 1/20

(52) U.S. Cl. .................. 424/251.1; 424/200.1; 424/190.1; 424/185.1; 424/184.1; 536/23.1; 536/23.7; 536/24.3; 536/24.32; 435/69.1; 435/69.3; 435/69.7; 435/252.3; 435/320.1; 435/325

(58) Field of Search .................. 424/184.1, 185.1, 424/190.1, 200.1, 251.1; 536/23.1, 23.7, 24.3, 24.32; 435/69.1, 69.3, 69.7, 252.3, 320.1, 325

(56) References Cited

U.S. PATENT DOCUMENTS

| | | | |
|---|---|---|---|
| 5,292,869 A | | 3/1994 | Schryvers |
| 5,972,657 A | | 10/1999 | Murphy et al. |
| 6,004,562 A | | 12/1999 | Campagnari et al. |
| 6,090,576 A | * | 7/2000 | Myers .................. 435/69.1 |
| 6,190,668 B1 | | 2/2001 | Yang et al. |
| 6,290,970 B1 | | 9/2001 | Yang et al. |

FOREIGN PATENT DOCUMENTS

| | | | | |
|---|---|---|---|---|
| CA | WO 90/12591 | * | 11/1990 | ......... A61K/39/095 |
| WO | WO 90/12591 | | 4/1990 | |
| WO | WO 97/13785 | | 4/1997 | |
| WO | WO 97/32980 | | 9/1997 | |

OTHER PUBLICATIONS

Bowie et al. Science, vol. 247: 1990; p. 1306; p. 1308.*
Houghten et al. (Vaccines, 1986, Edited by Fred Brown: Cold Spring Harbor Laboratory.*
Yu et al 1993; Microbial pathogenesis, 15; 433–445.*
AEBI, C, et al., "Expression of the CopB Outer Membrane Protein by *Moraxella catarrhalis* Is Regulated by Iron and Affects Iron Acquisition from Transferrin and Lactoferrin" *Infection and Immunity*, Jun. 1996, 64:2024–2030.
Bartos, L. C. and T.F. Murphy, "Comparison of the outer membrane proteins of 50 strains of Branhamella catarrhalis" *Journal of Infectious Diseases*, Oct. 1988, 158(4):761–765.
Bonnah, R. A., et al., Biochemical analysis of lactoferrin receptors in the Neisseriaceae: identification of a second bacterial lactoferrin receptor protein, *Microbial Pathogenesis* 1995, 19:285–297
Campagnari, A. A, et al. "Growth of *Moraxella catarrhalis* with Human Transferrin and Lactoferrin: Expression of Iron–Repressible Proteins without Siderophore Production" *Infection and Immunity*, Nov. 1994, 62:4909–4914.
Campagnari, A. A., et al. "Outer Membrane Protein B1, an Iron–Repressible Protein Conserved in the Outer Membrane of *Moraxella (Branhamella) catarrhalis*, Binds Human Transferrin" *Infection and Immunity*, Sep. 1996, 64:3920–3924.
Chen, D., et al., "Antibodies to the UspA Outer Membrane Protein of *Moraxella catarrhalis* Block Bacterial Attachment in vitro and Are Protective in a Murine Pulmonary Challenge Model" *Abstracts of the 95th General Meeting of the American Society for Microbiology 1995*, 290.
Chen, D., et al., "Evaluation of Purified UspA from *Moraxella catarrhalis* as a Vaccine in a Murine Model after Active Immunization" *Infection and Immunity*, Jun. 1996, 64:1900–1905.
Danve, B., et al. "Transferrin–binding proteins isolated from *Neisseria meningitidis* elicit protective and bactericidal antibodies in laboratory animals" *VACCINE*, 11:1214–1220, 1993.
Gerlach, G.F. et al. "Characterization of Two Genes Encoding Distinct Transferrin–Binding Proteins in Different *Actinobacillus pleuropneumoniae* Isolates" *Infection and Immunity*, Aug. 1992, 60:3253–3261.
Gary–Owen, S.D. and Schryvers, A. B. "Bacterial transferrin and lactoferrin receptors" *Trends in Microbiology*, May 1996, 187(4):185–191.
Helminen M. E., et al., "A Large, Antigenically Conserved Protein on the Surface of *Moraxella catarrhalis* Is a Target for Protective Antibodies" *The Journal of Infectious Diseases* 1994, 170:867–72.

(List continued on next page.)

*Primary Examiner*—Lynette R. F. Smith
*Assistant Examiner*—Padmavathi Baskar
(74) *Attorney, Agent, or Firm*—Bill T. Brazil; Alan M. Gordon; Wyeth

(57) ABSTRACT

A protein from the *M. catarrhalis* designated the 74 kD protein is isolated and purified. The 74 kD protein has an amino-terminal amino acid sequence which is conserved among various strains of *M. catarrhalis*. The protein has a molecular weight of approximately 74,9 kD as measured on a 10% SDS-PAGE gel, while its molecular weight as measured by mass spectrometry is approximately 74 kD. The 74 kD protein is used to prepare a vaccine composition which elicits a protective immune response in a mammalian host to protect the host again disease caused by *M. catarrhalis*.

10 Claims, 9 Drawing Sheets

OTHER PUBLICATIONS

Helminen M. E., et al., "A Major Outer Membrane Protein of *Moraxella catarrhalis* Is a Target for Antibodies That Enhance Pulmonary Clearance of the Pathogen in an Animal Model" *Infection and Immunity*, May 1993, 61:2003–2010.

Helminen M. E., et al., "Human Immune Response against Outer Membrane Proteins of *Moraxella (Branhamella) catarrhalis* Determined By Immunoblotting and Enzyme Immunoassay" *Clinical and Diagnostic Laboratory Immunology*, Jan. 1995, 2:35–39.

Lissolo, L. et al., "Evaluation of Transferrin–Binding Protein 2 within the Transferrin–Binding Protein Complex as a Potential Antigen for Future Meningococcal Vaccines" *Infection and Immunity*, Mar. 1995, 63:884–890.

Maciver, I, et al. "Effect of Immunization on Pulmonary Clearance of *Moraxella catarrhalis* in an Animal Model" *The Journal of Infectious Diseases* 1993, 168:469–72.

Mathers, K. E., et al., "Characterisation of an outer membrane protein of *Moraxella Catarrhalis*" *FEMS Immunology and Medical Microbiology*, 1997, 19: 231–236.

Mathers, K. E., et al. "Characterisation of an outer membrane protein from *Moraxella Catarrhalis*" *ICAAL*, 1997.

Myers, L. E., et al., "The Transferrin Binding Protein B of *Moraxella catarrhalis* Elicits Bactericidal Antibodies and Is a Potential Vaccine Antigen" *Infection and Immunity*, Sep. 1998, 66:4183–4192.

Ogunnariwo, J. A, and A. B. Schryvers "Rapid Identification and Cloning of Bacterial Transferrin and Lactoferrin Receptor Protein Genes" *Journal of Bacteriology*, Dec. 1996, 24:7326–7328.

Schryvers A. B. and B. C. Lee, "Comparative analysis of the transferrin and lactoferrin binding proteins in the family *Neisseriaceae*" *Can. J. Microbiol.* 1989, 35:409–415.

Sethi, S. et al., "Serum Antibodies to Outer Membrane Proteins (OMPs) of *Moraxella (Branhamella) catarrhalis* in Patients with Bronchiectasis: Identification of OMP B1 as an Important Antigen" *Infection and Immunity*, Apr. 1995, 63:1516–1520.

Unhanand, M., et al. "Pulmonary Clearance of *Moraxella catarrhalis* in an Animal Model" *Journal of Infectious Deseases*, 1992; 165:644–50.

Verghese A., et al. "Pulmonary Clearance and Phagocytic Cell Response in a Murine Model of *Branhamella catarrhalis* Infection" *The Journal of Infectious Diseases* 1990, 62:1189–1192.

Yu, R., "The interaction between human transferrin and transferrin binding protein 2 from Moraxella(Branhamella) catarrhalis differs from that of other human pathogens" *Microbial Pathogenesis*, 1993,15:433–445.

* cited by examiner

SEQUENCE LISTING

<160> NUMBER OF SEQ ID NOS: 9

<210> SEQ ID NO 1
<211> LENGTH: 13
<212> TYPE: PRT
<213> ORGANISM: Moraxella catarrhalis
<220> FEATURE:
<221> NAME/KEY: unsure
<222> LOCATION: 1

```
<223> OTHER INFORMATION: uncertainties in the sequence

<400> SEQUENCE: 1

Xaa Gly Gly Ser Gly Gly Ser Asn Pro Pro Ala Pro Thr
 1               5                  10

<210> SEQ ID NO 2
<211> LENGTH: 17
<212> TYPE: PRT
<213> ORGANISM: Moraxella catarrhalis
<220> FEATURE:
<221> NAME/KEY: unsure
<222> LOCATION: 1
<223> OTHER INFORMATION: uncertainties in the sequence

<400> SEQUENCE: 2

Xaa Gly Gly Ser Gly Gly Ser Asn Pro Pro Ala Pro Thr Pro Ile Pro
 1               5                  10                  15

Asn

<210> SEQ ID NO 3
<211> LENGTH: 20
<212> TYPE: PRT
<213> ORGANISM: Moraxella catarrhalis
<220> FEATURE:
<221> NAME/KEY: unsure
<222> LOCATION: 1
<223> OTHER INFORMATION: uncertainties in the sequence

<400> SEQUENCE: 3

Xaa Gly Gly Ser Gly Gly Ser Asn Pro Pro Ala Pro Thr Pro Ile Pro
 1               5                  10                  15

Asn Ala Ser Gly
            20

<210> SEQ ID NO 4
<211> LENGTH: 27
<212> TYPE: PRT
<213> ORGANISM: Moraxella catarrhalis
<220> FEATURE:
<221> NAME/KEY: unsure
<222> LOCATION: 1
<223> OTHER INFORMATION: uncertainties in the sequence

<400> SEQUENCE: 4

Xaa Gly Gly Ser Gly Gly Ser Asn Pro Pro Ala Pro Thr Pro Ile Pro
 1               5                  10                  15

Asn Ala Ser Gly Ser Gly Asn Thr Gly Asn Thr
            20                  25

<210> SEQ ID NO 5
<211> LENGTH: 18
<212> TYPE: PRT
<213> ORGANISM: Moraxella catarrhalis
<220> FEATURE:
<221> NAME/KEY: unsure
<222> LOCATION: 1
<223> OTHER INFORMATION: uncertainties in the sequence

<400> SEQUENCE: 5

Xaa Gly Gly Ser Gly Gly Ser Asn Pro Pro Ala Pro Thr Pro Ile Pro
 1               5                  10                  15

Asn Ala

<210> SEQ ID NO 6
```

```
<211> LENGTH: 14
<212> TYPE: PRT
<213> ORGANISM: Moraxella catarrhalis

<400> SEQUENCE: 6

Thr Asp Glu Lys Asn Lys Pro Asp Gly Tyr Asn Gly Glu Tyr
 1               5                  10

<210> SEQ ID NO 7
<211> LENGTH: 15
<212> TYPE: PRT
<213> ORGANISM: Moraxella catarrhalis

<400> SEQUENCE: 7

Asn Gly Glu Tyr Gly His Ser Ser Glu Phe Thr Val Asn Phe Lys
 1               5                  10                  15

<210> SEQ ID NO 8
<211> LENGTH: 14
<212> TYPE: PRT
<213> ORGANISM: Moraxella catarrhalis

<400> SEQUENCE: 8

Thr Asp Glu Lys Asn Lys Pro Asp Gly Tyr Asn Gly Glu Tyr
 1               5                  10

<210> SEQ ID NO 9
<211> LENGTH: 20
<212> TYPE: PRT
<213> ORGANISM: Moraxella catarrhalis

<400> SEQUENCE: 9

Lys Ser Ile Val Ile Arg Asp Ala Asp Val Thr Gly Gly Phe Tyr Tyr
 1               5                  10                  15

Pro Asn Ala Thr
            20
```

US 6,461,618 B1

74 KILODALTON OUTER MEMBRANE PROTEIN FROM *MORAXELLA CATARRHALIS*

This application claims priority from PCT application, PCT/US98/01840, filed Jan. 29, 1998, which claims priority from provisional application Ser. No. 60/036,827, filed Jan. 31, 1997, the entire disclosures of which are hereby incorporated by reference.

FIELD OF THE INVENTION

This invention relates to an approximately 74,000 Dalton (74 kD) outer membrane protein purified from *Moraxella catarrhalis*.

BACKGROUND OF THE INVENTION

*Moraxella* (Branhamella) *catarrhalis* is one of the major bacterial pathogens causing otitis media in children (Bibliography entries 1,2,3,4). It also causes sinusitis, laryngitis, tracheitis, pneumonia, and other respiratory diseases in children and adults (5,6,7). A prophylactic vaccine is clearly needed because nearly all clinical isolates are resistant to β-lactam antibiotics (8,9).

The outer membrane proteins (OMPs) of *M. catarrhalis* are being investigated as potential vaccine candidates because they are readily accessible to antibodies. Indeed, antibodies elicited in mice towards certain OMP's including UspA and the CopB have already been shown to have biological activity, such as bactericidal activity, adhesion blocking activity and enhanced pulmonary clearance of the bacteria in an animal model (10,11,12,13). Serology data from humans who have suffered a recent *M. catarrhalis* infection indicates that humans develop antibodies towards OMP's following natural infection (14,15,16,17,18). This suggests that OMP's are the targets of the host's defense mechanisms. UspA-specific antibodies are present in normal human serum and these antibodies have bactericidal activity. There are also high levels of antibodies towards OMPs of approximately 80 kD in sera from both healthy humans and patients recovering from recent *M. catarrhalis* infections (16). Several proteins from *M. catarrhalis* migrate within this size range. Among them are CopB (12), the B1 protein (18), a transferrin binding protein (TbpB) and a lactoferrin binding protein (LbpB) (19) Whether these proteins are the same or different from one another has yet to be determined. None of them, however, has been evaluated in a purified form for vaccine use.

An efficacious vaccine to protect against diseases caused by *M. catarrhalis* should confer protection at all stages of disease. These stages include bacterial colonization on mucosal surfaces, bacterial multiplication, spread and invasion, and the development of inflammatory response. Multiple bacterial components may be required to formulate an efficacious vaccine. Although there is pre-clinical data to suggest that some surface components of *M. catarrhalis* are potential vaccine antigens, it is as yet unclear if these components will confer sufficient protective immunity in humans. Thus, it is important to identify and evaluate new bacterial antigens for vaccine use.

SUMMARY OF THE INVENTION

Accordingly, it is an object of this invention to isolate, purify and characterize an additional protein from *M. catarrhalis*. It is a further object of this invention to test whether this protein is a viable vaccine candidate in appropriate model systems.

These and other objects of the invention as discussed below are achieved by the isolation and purification of a protein from *M. catarrhalis* which is designated the 74 kD protein, based on approximate molecular weight as measured by mass spectrometry, as well as peptides of the 74 kD protein comprising an epitope or epitopes thereof. The isolated and purified 74 kD protein from *M. catarrhalis* has an amino-terminal amino acid sequence which is conserved among various strains of *M. catarrhalis*. This amino-terminal amino acid sequence comprises the sequence Xaa Gly Gly Ser Gly Gly Ser Asn Pro Pro Ala Pro Thr (SEQ ID NO:1), where the first residue is not identified, or a biologically equivalent amino-terminal amino acid sequence thereof. The protein of this invention has a molecular weight of approximately 74.9 kD as measured on a 10% SDS-PAGE gel, while its molecular weight as measured by mass spectrometry is approximately 74 kD.

In another embodiment of this invention, the isolated and purified 74 kD protein or a peptide of the 74 kD protein comprising an epitope or epitopes thereof, is used to prepare a vaccine composition which elicits a protective immune response in a mammalian host. The vaccine composition may further comprise an adjuvant, diluent or carrier. Examples of such adjuvants include aluminum hydroxide, aluminum phosphate, MPL™, Stimulon™ QS-21, and IL-12. The vaccine composition is administered to a mammalian host in an immunogenic amount sufficient to protect the host against disease caused by *M. catarrhalis*.

BRIEF DESCRIPTION OF THE FIGURES

FIG. 1 depicts the characterization of the purified 74 kD protein from O35E strain by SDS-PAGE and Western blots.

DETAILED DESCRIPTION OF THE INVENTION

Figures 1A, 1B, 1C:
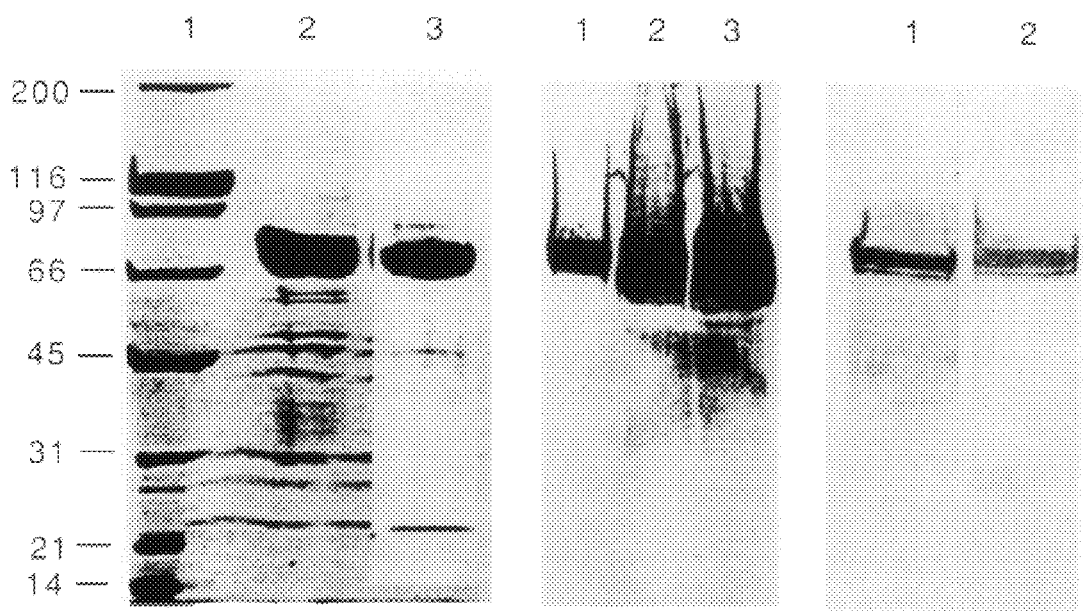
FIG. 1A depicts a Coomassie blue stained 4–15% SDS-PAGE showing enriched 74 kD protein eluted from the S column (lane 2) and hydroxyapatite column (lane 3). The molecular weight standards (lane 1:200 (myosin); 160 (β-galactosidase); 97 (phosphorylase); 66 (serum albumin); 45 (ovalbumin); 31 (carbonic anhydrase); 21 (trypsin inhibitor); 14 (lysozyme)) are in thousands.
FIG. 1B depicts purified 74 kD protein by silver staining; the loading was 3 μg (lane 1), 15 μg (lane 2) and 30 μg (lane 3).
FIG. 1C depicts western blots detected with either mouse antiserum against the purified 74 kD protein (lane 1) or MAb 72-32 (lane 2).

This invention relates to an isolated and purified *M. catarrhalis* protein designated the 74 kD protein. This 74 kD protein has an amino-terminal amino acid sequence which is conserved among the three strains examined of *M. catarrhalis*. The protein of this invention has a molecular weight of approximately 74.9 kD as measured on a 10% SDS-PAGE gel, while its molecular weight as measured by mass spectrometry is approximately 74 kD. The amino acid composition of the protein has also been determined. The invention relates further to peptides of the 74 kD protein comprising an epitope or epitopes thereof. Such peptides incorporate one or more epitopes that are immunologically cross-reactive with one or more epitopes of the 74 kD protein. Such peptides are first generated and then tested for cross-reactivity.

Initially, the 74 kD protein was purified from salt wash vesicles made from O35E strain and evaluated in mice. Preliminary results indicated that the 74 kD protein is surface exposed, in that the mouse antisera had bactericidal activity, and immunized mice exhibited enhanced clearance of the *M. catarrhalis* in a murine challenge model. However, this particular 74 kD preparation was contaminated with lipooligosaccharide (LOS) which also induced an antibody response in mice. Subsequently, the 74 kD protein was purified from three strains of *M. catarrhalis* by a modified procedure. These preparations lacked detectable LOS or other protein contamination. Example 1 below describes the new purification method, which involves the extraction of the protein directly from whole bacterial cells from *M. catarrhalis* strains O35E and 430-345, followed by a series of column chromatography steps. A modified version of this method was also used to purify the 74 kD protein from TTA24 strain.

The 74 kD protein migrates slightly more slowly on a 4–15% gradient SDS-PAGE than CopB, another *M. catarrhalis* protein (data not shown). SDS-PAGE analysis using a 10% w/v acrylamide gel provided an estimated molecular weight for this protein of approximately 74.9 kD (see Example 4). The actual molecular mass as determined by mass spectrometry was approximately 74 kD (see Example 4). The N-terminal sequences from O35E, TTA24 and 430-345 strains were found to be identical to the extent of sequencing of these strains, that is, for the first 18 residues (see Examples 6 and 7).

Two alternative methods for the purification of the 74 kD protein were also employed. For both methods, the salt wash vesicles, prepared as previously described (11), were suspended in a 0.5% Triton X-100™ and 10 mM N-[hydroxyethyl]piperazine-N'-[2-ethanesulfonic acid] (HEPES) buffer and incubated for one hour at room temperature. The suspension was centrifuged at low speed (10,000×g for 20 minutes) at 4° C. to remove particulates. For the first method, the supernatant was passed over a DEAE Sepharose® (Pharmacia, Piscataway, N.J.) column equilibrated with the same buffer. A single band of 74 kD protein, as seen by SDS-PAGE, eluted in the flow through and in the buffer wash, while contaminants eluted upon increasing the salt (NaCl) concentration. For the second method, the supernatant was passed over a CM Sepharose® column equilibrated with the same Triton X-100™-HEPES buffer. The proteins on this column were then eluted with a step gradient of increasing salt concentration. The 74 kD protein, which eluted at 200 mM of NaCl, migrated as a single band. Only two major outer membrane proteins from salt wash vesicles, the 74 kD protein and the CopB protein, migrate at about this size on SDS-PAGE. The 74 kD protein failed to react by western blotting with a monoclonal antibody 10F3 specific for the CopB protein. Minor amounts of the C/D protein present can be removed by using an additional ion exchange column.

This invention also comprises polypeptides whose amino-terminal sequences differ from those of the 74 kD protein, but are biologically equivalent to those described for that protein. Such polypeptides may be said to be biologically equivalent to the 74 kD protein if their sequences differ only by minor deletions from or conservative substitutions to the amino acid sequence, such that the tertiary configurations of the sequences are essentially unchanged from those of the 74 kD protein and biological activity is retained.

For example, alanine, a hydrophobic amino acid, may be substituted by another less hydrophobic residue, such as glycine, or a more hydrophobic residue, such as valine, leucine, or isoleucine. Similarly, substitution of one negatively charged residue for another, such as aspartic acid for glutamic acid, or one positively charged residue for another, such as lysine for arginine, as well as changes based on similarities of residues in their hydropathic index, can also be expected to produce a biologically equivalent product. Each of the proposed modifications is well within the routine skill in the art, as is determination of retention of biological activity of the encoded products. Therefore, where the term "74 kD protein" is used in either the specification or the claims, that term will be understood to encompass all such modifications and variations which result in the production of a biologically equivalent protein.

The N-terminus from the O35E strain and two internal peptides from a chymotrypsin digest of the same protein were determined and found to have no homology with any other known protein from *M. catarrhalis* in searches of the GenBank CDS translations, PDB, SwissProt, Spupdate and PIR databases with Basic Local Alignment Search Tool (BLAST) (20). However, the two internal peptides have significant sequence homology to the transferrin binding protein from *N. meningitidis* and *H. influenzae* (see Example 8). The amino acid composition of the 74 kD protein is set forth in Example 5.

Purified 74 kD proteins from strains O35E and 430-345 were immunogenic in mice and their antibodies reacted with the homologous strain by whole-cell ELISA; however, the whole-cell titers toward heterologous strains varied considerably (see Example 12). The 74 kD protein from TTA24 strain appeared to be better conserved, because antibodies made to this protein exhibited moderately high reactivity to heterologous strains by whole cell ELISA (Example 12). Antisera against the purified proteins from all three strains had complement-dependent bactericidal activity toward all heterologous strains (see Example 9). This suggests that antibodies towards the conserved epitopes are important.

The level of antibodies reactive to heterologous strains and bactericidal antibody titers were improved by using certain adjuvants such as Stimulon™ QS-21 (Aquila Biopharmaceuticals, Inc., Worcester, Mass.) or a mixture of MPL™ (3-O-deacylated monophosphoryl lipid A; RIBI ImmunoChem Research, Inc., Hamilton, Mont.) and aluminum phosphate (see Examples 10 and 11). Mice immunized with the 74 kD proteins purified from strains O35E and 430-345 exhibited strong pulmonary clearance of the O35E strain toward which the antibodies reacted with high titers (P<0.01), but not the TTA24 strain toward which the sera reacted poorly (see Example 13). Further, normal human sera contain naturally acquired antibodies towards the conserved epitopes on the 74 kD proteins from both O35E and TTA24 strains (Example 14). This suggests that *M. catarrhalis* expresses this protein in vivo and that the 74 kD protein is a target of the immune response upon natural infection. These human antibodies reacted better to purified 74 kD protein from TTA24 strain than protein from O35E strain (see Example 15). This suggests that the 74 kD protein from TTA24 strain is conserved.

The relationship of the 74 kD protein to other proteins will now be described. Eight major outer membrane proteins from *M. catarrhalis* were initially described by Bartos and Murphy, who designated these OMPs A–H in the order of decreasing molecular weight (21). Two additional outer membrane proteins, designated UspA (13) and B1 (18), were described later. The OMP B was renamed B2 after the discovery of B1 (18). Except for their similarity in molecular mass, the B1 and B2 proteins are unrelated. OMP B2 is probably the same protein as CopB described by Helminen et al. (12). This protein has a molecular mass of 82 kD, and appears to play a role in iron acquisition (22).

The 74 kD protein described in this application is distinct from the CopB protein in two aspects. First, a monoclonal antibody (MAb) designated 72-32, which reacts with the 74 kD protein, did not react with a recombinant CopB made in *E. coli* on western blot (data not shown). Nor did a CopB specific MAb, 10F3, react with the purified 74 kD protein in the same assay. Second, the N-terminal amino acid sequence and two internal peptide sequences of the 74 kD protein were not found in the predicted protein sequence deduced from the published gene sequence of CopB (12).

The 74 kD protein of this invention is most similar to the B1 protein in terms of size and the degree of antigenic conservation. The OMP B1 was initially described by Sethi et al. (18), who did not isolate or purify the protein. Sethi et al. noted the consistent presence of polyclonal antibodies towards an 74 kD minor protein in sera from patients with bronchiectasis. They also reported that B1 protein had surface exposed epitopes and appeared to be antigenically variable among strains of *M. catarrhalis*. The level of B1 expression was up-regulated under iron-limiting culture conditions for some isolates (23). There are also reports that the B1 protein binds transferrin (24). These reports suggested that the B1 protein may be involved in iron acquisition and utilization. The usefulness of the B1 protein as a vaccine antigen was not investigated in these reports. In contrast, the data presented in this application did not show significant changes in 74 kD protein expression levels by either depleting or supplementing iron in the culture broth (see Example 3).

Like B1 protein, the 74 kD protein binds transferrin (see Example 3). Transferrin-binding proteins have been detected in several bacterial species, including *M. catarrhalis*. Using transferrin and lactoferrin affinity columns, Bonnah et al. identified two distinct receptor proteins from *M. catarrhalis* with molecular weight masses of approximately 80 kD (19). This is the same range as for the proteins designated B1 and CopB. Unfortunately, these reports did not provide enough information on the biochemical, immunological and molecular aspects of these proteins to allow the identification of the 74 kD protein as either of these proteins. However, many of the properties of the TbpB from the Neisseria family and *Haemophilus influenzae* are similar to those of the 74 kD protein from *M. catarrhalis*. These include the ability to bind transferrin in both native or denatured form and antigenic heterogeneity.

However, the 74 kD protein of *M. catarrhalis* differs from the TbpB protein of Neisseria in several respects. First, the molecular weight of the 74 kD protein is relatively well conserved from strain to strain, while the molecular weight of TbpB in Neisseria varies from strain to strain (25). Second, mouse antibodies made against the 74 kD protein from TTA24 strain reacted with all strains of *M. catarrhalis* by whole cell ELISA, and were bactericidal toward all strains assayed. In contrast, antibodies to TbpB of Neisseria reacted only with a fraction of strains by ELISA and were only bactericidal toward strains to which the antibodies bound (26). Finally, the expression level of the 74 kD protein appears to be constitutive, while TbpB (from both Neisseria and Haemophilus), like the B1 protein, is iron repressed. Therefore, without further information, it is unclear whether the 74 kD protein, the B1 protein and TbpB protein are all the same protein.

Having isolated and characterized the 74 kD protein, the next step is to evaluate its potential as a vaccine antigen. Several lines of evidence presented in this application indicate that the 74 kD protein is a potential vaccine antigen candidate. First, as detailed in Example 2 below, it contains surface exposed epitopes. This is important, because only surface exposed epitopes are accessible to the antibodies. The epitope recognized by the MAb 72-32, although not conserved among all isolates, is surface exposed. Further, both the antibodies toward the 74 kD protein purified from the human sera and antibodies made to the purified protein in mice reacted with several strains of *M. catarrhalis* by whole cell ELISA. Some of the epitopes are clearly conformational, since many of the monoclonal antibodies react with purified 74 kD protein and whole bacterial cells by ELISA, but do not react with the denatured 74 kD protein on western blot. It also suggests that the purified protein retains at least some conformational epitopes.

Second, some surface exposed epitopes of the 74 kD protein are conserved among strains of *M. catarrhalis*. An efficacious vaccine needs to confer protective immunity against most, if not all, strains. Because the expression of the protein appears to vary from isolate to isolate in vitro (see Example 3), the degree of antigenic variation of the 74 kD protein among *M. catarrhalis* strains has been difficult to assess. Nevertheless, it is evident that the 74 kD protein contains conserved epitopes. Antibodies to the 74 kD protein, whether produced in mice or developed in humans following natural infection, were bound by whole bacterial cells of the heterologous strains. The 74 kD protein from TTA24 strain is fairly conserved, whereas the 74 kD protein from two other strains studied is either less conserved or the strain-specific epitopes are more immunogenic than the conserved epitopes. Current data seems to suggest that the 74 kD protein from TTA24 strain may have more potential as a vaccine antigen because it elicits highly cross-reactive antibodies toward heterologous strains (see Example 12, Table 9).

Third, antibodies toward conserved surface epitopes elicited by the purified protein were bactericidal (see Example 9). Although it is unclear how antibodies mediate protection against infections by *M. catarrhalis*, they could play a role in a number of pathways. These include inhibition of bacterial adherence, interference of nutrient uptake, opsonic phagocytosis and complement-dependent killing. It was observed that adults, a population usually resistant to *M. catarrhalis* infections, have a significantly higher level of serum bactericidal activity to *M. catarrhalis* than children, a population susceptible to *M. catarrhalis* infections (data not shown). The finding that mouse antisera to the 74 kD protein exhibit bactericidal activity toward heterologous strains in a antibody concentration-dependent manner suggests that this protein is a protective antigen. Clearly, the conserved epitope of the 74 kD protein is an important target of the bactericidal antibodies.

Finally, mice immunized with the 74 kD protein exhibited enhanced pulmonary clearance of the bacteria in the murine challenge model (see Example 13). Although the mechanisms of bacterial clearance in this model are unknown, antibodies clearly play an important role in this model (27). In addition to the 74 kD protein described in this application, UspA and CopB have been shown to promote enhanced clearance in this model (11,12,13). Further, only antibodies to certain epitopes of these proteins appear to enhance bacterial clearance. Thus, the model has been useful for selecting vaccine candidates that may elicit antibodies with in vivo biological activity. Two strains of the bacteria are suitable for challenge in the murine pulmonary model, and both were tested. Enhanced bacterial clearance was seen for O35E strain which exhibited strong reactivity with the antibodies against the 74 kD protein prepared from two different strains. Homologous clearance of strain TTA24 was seen; however, heterologous clearance was not observed. This is probably because of the poor antibody reactivity toward this isolate elicited by the purified protein. It remains to be determined whether the 74 kD protein from TTA24 strain will promote enhanced clearance of heterologous strains in this challenge model.

Another potential mechanism by which the 74 kD protein can confer protection in humans is by eliciting antibodies that block iron uptake by *M. catarrhalis*. Iron is an essential element for the bacteria to grow and cause pathogenesis in vivo. However, the concentration of free iron in the extracellular environment is too low to support bacterial growth. Extracellular iron is virtually all sequestered in host proteins such as lactoferrin on the mucosal surface and transferrin in the serum. Several bacterial species including *M. catarrhalis* can acquire iron from host proteins through their specialized surface receptors, such as transferrin binding proteins (TbpA and B) and lactoferrin binding proteins (Lbp A and B). To obtain iron, TbpB, a lipoprotein that is an outer membrane protein, functions as a receptor for transferrin in body fluids.

It has been shown that *M. catarrhalis* can utilize transferrin as the sole iron source for growth in vitro (19), and this may be an important mechanism of iron acquisition in vivo. The mechanism by which *M. catarrhalis* acquires iron from transferrin is not clear; however, it very likely requires direct interaction of Tbp with transferrin. Example 16 indicates that antibodies to the 74 kD protein from *M. catarrhalis* are able to specifically block transferrin binding by the bacterial lysates. This is consistent with previous findings that antibodies to the meningococcal TpbB were able to lower the growth rate of meningococci when human transferrin was the sole iron source (28).

The transferrin binding proteins from other species are reported to be lipoproteins (29,30). This usually blocks the protein's N-terminus, preventing the determination of the N-terminal sequence (31). Because an N-terminal sequence could be determined for the 74 kD protein from three strains, this represents another possible difference between the transferrin binding protein and the 74 kD protein of *M. catarrhalis*.

Therefore, the 74 kD protein and peptides of the 74 kD protein comprising an epitope or epitopes thereof are useful in the preparation of vaccines to confer protection to humans against otitis media and other diseases caused by *M. catarrhalis*.

These vaccine compositions comprise the isolated and purified 74 kD protein of *M. catarrhalis* or a peptide of the 74 kD protein comprising an epitope or epitopes thereof, wherein the vaccine composition elicits a protective immune response in a mammalian host.

Vaccines containing the 74 kD protein or peptides may be mixed with immunologically acceptable diluents or carriers in a conventional manner to prepare injectable liquid solutions or suspensions. In addition, the vaccines may include aluminum hydroxide, aluminum phosphate (alum) or other pharmaceutically acceptable adjuvants, such as Stimulon™ QS-21 (Aquila Biopharmaceuticals, Inc. Worcester, Mass.), MPL™, and IL-12 (Genetics Institute, Cambridge, Mass.).

The vaccines of this invention may also include additional *M. catarrhalis* proteins which are known in the art. Examples of such proteins are those designated CopB, UspA, C/D and E.

The vaccines of this invention further include other protective agents which are coupled to the 74 kD protein or peptides, such that the 74 kD protein or peptides function as a carrier molecule. For example, agents which protect against other pathogenic organisms, such as bacteria, viruses or parasites, are coupled to the 74 kD protein or peptides to produce a multivalent vaccine useful in the prevention of both *M. catarrhalis* infection and other pathogenic infections. In particular, the 74 kD protein or peptides can serve as immunogenic carriers by being conjugated to Haemophilus, meningococcal or pneumococcal polysaccharides or oligosaccharides. In addition, the 74 kD protein or peptides are coupled to another antigenic moiety of *M. catarrhalis* such as lipooligosaccharides.

The vaccines of this invention are administered by injection in a conventional manner, such as subcutaneous, intraperitoneal or intramuscular injection into humans, as well as by oral administration and intranasal administration, to induce an active immune response for protection against otitis media caused by *M. catarrhalis*. The dosage to be administered is determined by means known to those skilled in the art. Protection may be conferred by a single dose of vaccine, or may require the administration of several booster doses.

Normally, in the absence of human clinical data, active immunization in a recognized animal model is relied upon to predict the efficacy of a vaccine in humans. Here, the pulmonary clearance is measured in the murine challenge model. The murine challenge model permits an evaluation of the interaction of *M. catarrhalis* with the lower respiratory tract, as well as an assessment of pathologic changes in the lungs (32,33). This model reproducibly delivers an inoculum of bacteria to a localized peripheral segment of the murine lung. Bacteria multiply within the lung, but are eventually cleared as a result of host defense mechanisms and the development of a specific immune response.

In the present invention, the 74 kD protein is shown to be a viable vaccine candidate both because antibodies elicited by the 74 kD protein were bactericidal and because mice immunized with the 74 kD protein exhibited enhanced pulmonary clearance of M. catarrhalis in the murine challenge model.

The 74 kD protein or peptides thereof are also useful to produce polyclonal antibodies for use in passive immunization against *M. catarrhalis*. Polyclonal antisera are generated from animals immunized with the 74 kD protein or peptides thereof.

The 74 kD protein or peptides thereof are further used to generate monoclonal antibodies which may be used to diagnose the presence of *M. catarrhalis* in a clinical sample or a laboratory strain. The monoclonal antibodies react with *M. catarrhalis*, but not with other bacteria.

In order that this invention may be better understood, the following examples are set forth. The examples are for the purpose of illustration only and are not to be construed as limiting the scope of the invention.

EXAMPLES

Example 1

Purification and Characterization of the 74 kd Protein

Purification

The 74 kD protein was purified from strains O35E and 430–345 using the same procedure. The bacteria were grown in Fernbach flasks containing 1.3 liters of CY broth (10 g casamino acids, 15 g yeast extract per liter of distilled water) at 37° C. for 22 hours with shaking at 200 rpm. The bacteria were harvested by centrifugation (10,000×g for 20 minutes), resuspended in 50 ml of phosphate buffer (10 mM, pH 6.0) containing 0.1% Triton X-100™ (J.T. Baker Inc., Philipsburg, N.J.), and stirred for one hour at room temperature (RT). Particulates were removed by centrifugation (10,000×g, 60 minutes) and the soluble extract loaded on a 5 ml bed volume column of S Sepharose (Pharmacia, Piscataway, N.J.). The column was eluted with a NaCl step gradient in 10 mM phosphate buffer (pH 6.0) containing 0.1% Triton X-100™. The 74 kD protein was detected by dot blotting using MAb 72-32. Enriched fractions of the 74 kD protein (which eluted between 70–210 mM NaCl) were pooled, and applied to a 3 ml bed volume column of hydroxyapatite (BIO-RAD Laboratories). The column was washed with 10 mM phosphate buffer (pH 6.0) and eluted using a step gradient of phosphate buffer (pH 6.0). The 74 kD enriched fractions were pooled, concentrated using a Centriprep®-30 (Amicon, Beverly, Mass.), and passed over a column (2.6×100 cm) of Ultrogel AcA 44 (BioSepra Inc., Marlborough, Mass.) at a flow rate of 1.0 ml per minute in PBS (pH 7.4). The protein concentration was determined by a micro-bicinchoninic acid assay (Micro-BCA) (Pierce, Rockford, Ill.).

The 74 kD protein was purified from strain TTA24 by a slightly different procedure. The initial attempt to purify the 74 kD protein from TTA24 strain cultured in CY broth by the above method did not yield any protein. It was then observed that TTA24 cultured on Mueller-Hinton agar plates expressed a higher level of 74 kD protein. So, the bacteria grown on these plates were used as the starting material for purification. The protein did not bind to the S Sepharose® column under conditions used for the 74 kD protein from O35E. Instead, it was purified by sequential passage over first a hydroxyapatite column, then a Q High Performance column (Pharmacia) and finally an Ultrogel AcA44 column.

Characterization

The 74 kD protein was associated with bacterial cells cultured in CY broth. It was readily extracted in phosphate buffer (10 mM, pH 6.0) containing 0.1% Triton X-100™ after 1 h stirring at RT. The 74 kD proteins from strains O35E and 430–345 were among the few proteins in the whole cell extract that bound to the S column, and accounted for 50–70% of the total protein in the fractions that were eluted with 10 mM phosphate buffer (pH 6.0) containing 70–210 mM NaCl. It exhibited strong binding to a hydroxyapatite column and eluted with 500 mM phosphate buffer containing no detergent. The bulk of the contaminants were in the flow through fraction off this column. The major peak eluted off the AcA44 size-exclusion column contained a single homogenous band with a molecular mass of 74 kD on a Coomassie blue stained 4–15% acrylamide gradient SDS-PAGE.

The 74 kD protein from TTA24 strain was enriched by the HA column. It was among the few proteins which did not bind the Q column and was finally purified by the size exclusion column. The yield of purified proteins, as shown in Table 1 below was approximately 1–3 mg from 1.3 liter of broth culture.

TABLE 1

Purification of the 74 kD protein

| Bacterial strain | Culture volume | Final yield (mg) |
|---|---|---|
| O35E | 15 L | 24 |
| O35E | 20 L | 52 |
| 430-345 | 4 L | 4.48 |
| TTA24 | 20 plates (15 cm diameter) (2 L) | 6.3 |

The purified 74 kD proteins were analyzed by 4–15% gradient SDS-PAGE stained with Coomassie blue and silver staining. Reactivity to monoclonal antibodies and polyclonal mouse serum was determined by western blot (FIG. 1).

Example 2

Monoclonal Antibodies

The MAbs toward the 74 kD protein were made using the procedure of Chen et al. (11). In summary, mice (BALB/c) used for the fusion were immunized with outer membrane vesicles made from *M. catarrhalis* O35E strain. Hybridomas were first screened by ELISA against O35E whole bacterial cells. Those recognizing O35E whole cells were then tested for reactivity with purified 74 kD protein of the O35E strain by both ELISA and Western blotting. Reactivity toward heterologous strains was determined by whole-cell ELISA. The selected hybridomas were cloned by limiting dilution.

Two of the MAbs recognized the purified 74 kD protein by both ELISA and western blot. They did not react with the CopB protein. When the MAbs designated 72-32 and 81-8 were tested against six other *M. catarrhalis* strains by western blot analysis, they only reacted with the homologous isolate O35E. Thus, these two MAbs recognize strain specific epitopes. The lack of reactivity to heterologous strains was confirmed by whole cell ELISA.

Thereafter, all parent clones from that fusion were screened by ELISA. A dozen clones had reactivity to both the purified 74 kD protein and O35E whole bacterium cells, but none reacted to 11 heterologous strains. Only five of the 12 parent clones exhibited reactivity to the 74 kD protein on western blot. The non-reactors are probably directed against the conformational epitopes.

These data indicated that the 74 kD protein has surface exposed epitopes, and some of them may be conformational. It also indicated that the 74 kD protein from O35E strain is either antigenically heterogeneous or the strain-specific epitopes are more immunogenic than the conserved epitopes.

Example 3

Expression Level and Transferrin Binding Assay

There are indications that B1 protein (18) binds transferrin and it may be transferrin binding protein B (TbpB) (19). The 74 kD protein described herein appears to have similar molecular mass as well as the antigenic heterogeneity typical of TbpB.

Figure 2:
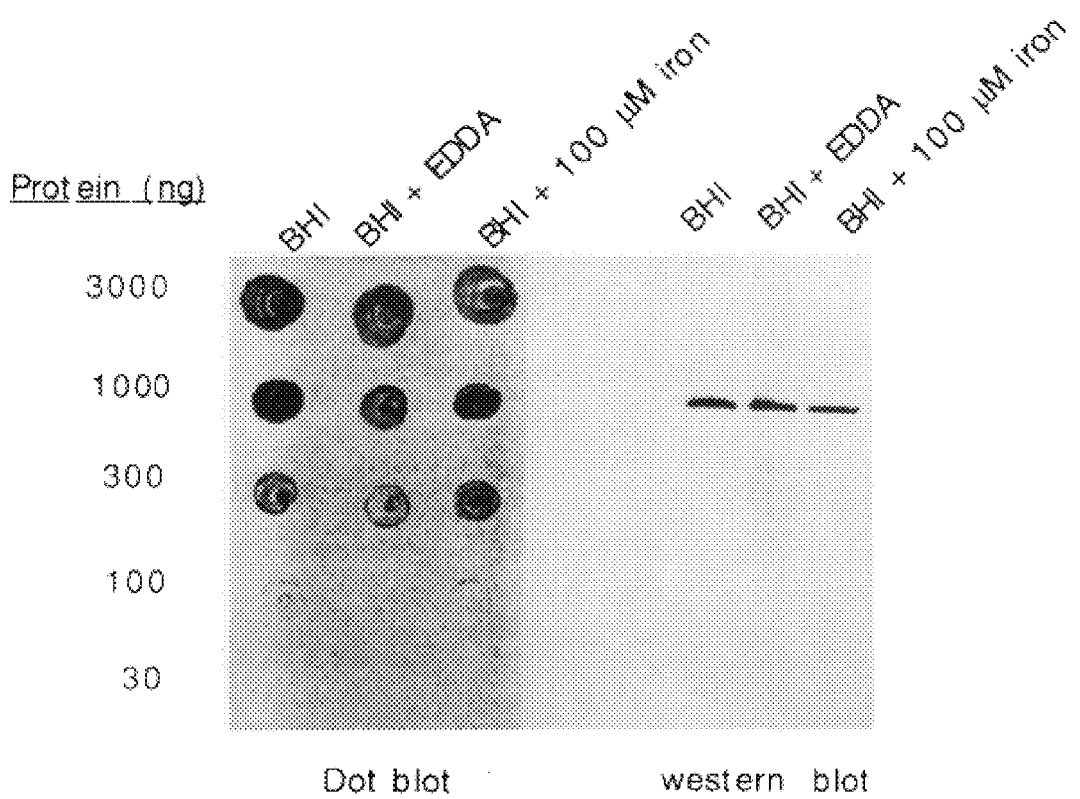
FIG. 2 depicts the expression level of 74 kD protein by O35E strain under different culture conditions. Bacteria were cultured in regular brain heart infusion (BHI), BHI supplemented with 10 mM ethylenediaminediacetate (EDDA) or 100 μM iron. Bacterial lysates applied to the membrane were detected by MAb 72-32 in dot blot and western blot assays.
Figure 3:
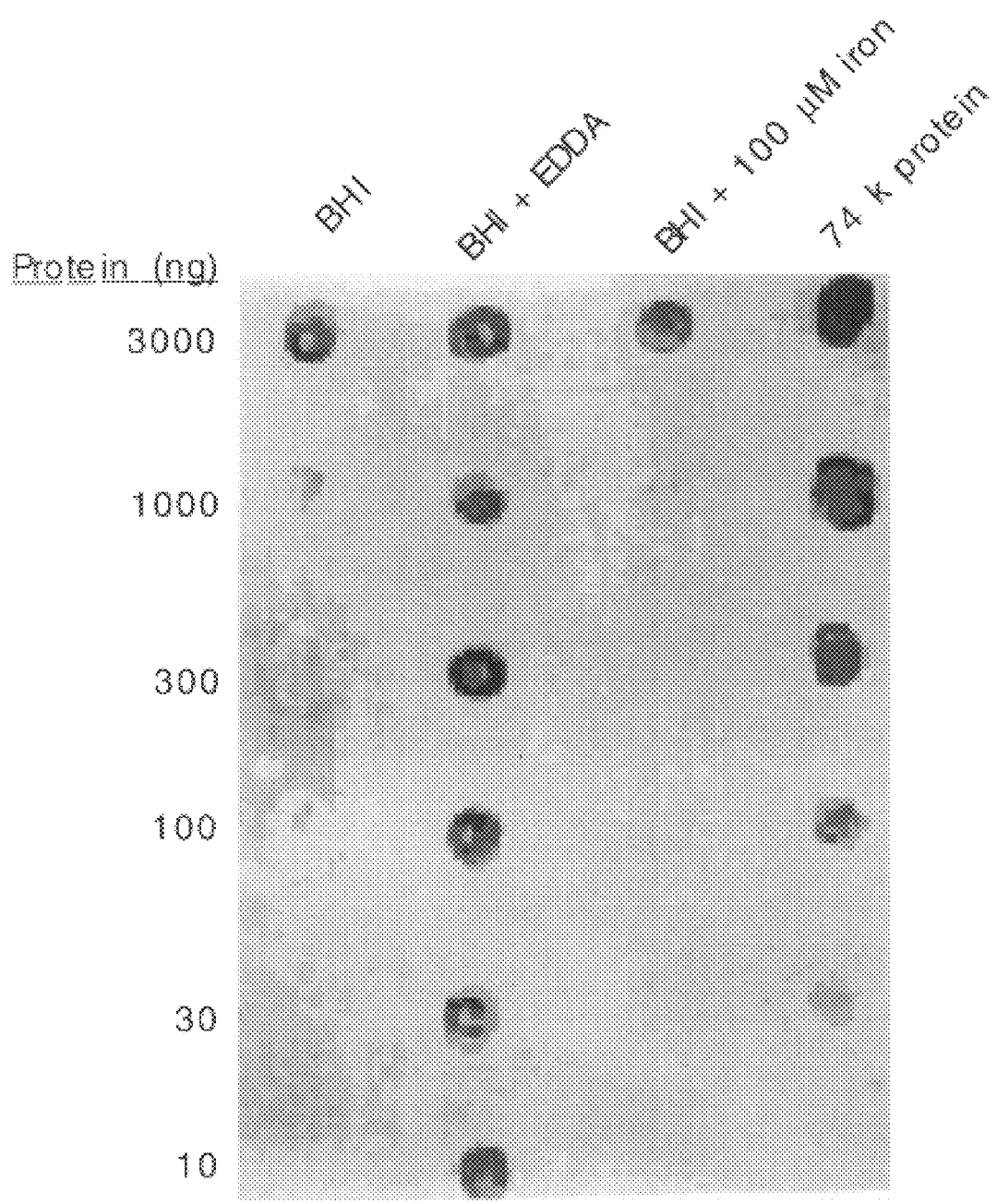
FIG. 3 depicts the expression of transferrin binding proteins by O35E strain under different culture conditions. Samples on the membrane were bacterial lysates as described for FIG. 2. Transferrin binding by the purified 74 kD protein is shown in the fourth column.

An initial test was performed to determine whether the purified 74 kD protein could bind transferrin. This was determined by probing purified 74 kD protein from strain O35E which was spot blotted on a nitrocellulose membrane with biotin-labeled transferrin. Strong reactivity was detected (see FIG. 3). Thus, transferrin binding is a common property of the 74 kD protein, B1 and TbpB. Since the expression level of transferrin binding proteins B1 and TbpB of *M. catarrhalis* is reported to depend on the iron content of the culture medium (18,19), the next step was to determine if the 74 kD expression level could be increased by depleting the iron in the culture broth. The methods used to deplete iron included both phosphate precipitation and chelation with EDDA. The 74 kD protein from the whole cell lysates was quantitated by dot blot and western blot using MAbs. There appeared to be no appreciable change in the expression level of the 74 kD protein in iron-depleted culture (see FIG. 2). However, the level of the transferrin binding proteins as determined by probing with biotin-labeled transferrin in a dot blot assay significantly increased in iron depleted culture (see FIG. 3). It is unknown whether this increase reflects changes in the ThpA or TbpB expression level. However, these preliminary results on the 74 kD expression level under iron limiting conditions are not consistent with the published reports for B1 and TbpB.

While the iron level did not appreciably affect expression, growth in different media did affect it. Lysates of bacteria adjusted to the same absorbance at 550 nm made from several strains of *M. catarrhalis* cultured in broth or on agar plates were probed with polyclonal antibodies against the purified 74 kD protein in a western blot. The polyclonal antibodies had been generated by immunizing mice with the 74 kD protein which had been purified from O35E strain. The 74 kD expression level appeared to be higher when the bacteria were cultured on an Mueller-Hinton agar plate than when cultured in broth culture (data not shown).

Figure 4:
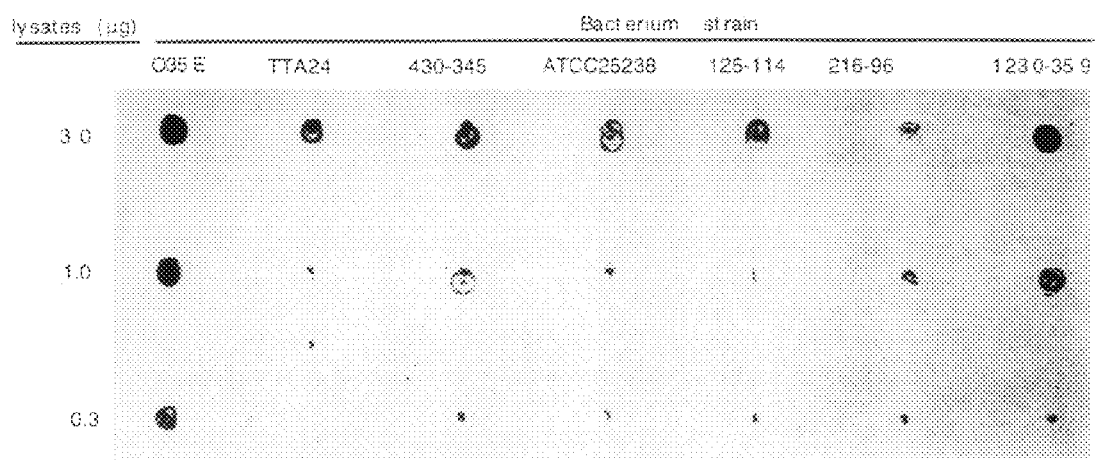
FIG. 4 depicts the variation in the expression level of 74 kD protein by *M. catarrhalis* strains. Bacterial lysates from seven strains of *M. catarrhalis* were titrated in 3-fold dilutions in a dot blot and detected with mouse polyclonal antibodies against the purified 74 kD protein from O35E strain (1:200).

The expression level of 74 kD protein appears to be strain dependent. When a low dilution of antiserum against 74 kD protein from O35E strain (1:200) was used in a dot blot assay to react with serially diluted whole cell lysates from seven *M. catarrhalis* strains, the strongest reactivity was seen towards strains O35E, 120–345 and 430–345. The reactivity toward the four other strains was three to nine fold less (see FIG. 4). Several attempts were made to purify the 74 kD protein from the strains exhibiting low reactivity, and only small amounts of the protein appeared to be present in these strains.

Example 4

Molecular Weight of the 74 kD Protein
Determination of Molecular Weight by SDS-PAGE Analysis The 74 kD protein purified from M. catarrhalis O35E was subjected to SDS-PAGE (10%, w/v, acrylamide) analysis (34) along with a wide-range of protein standards (Mark 12: apparent molecular weights of 200, 116.3, 97.4, 66.3, 55.4, 36.5, 31, 21.5, 14.4, 6, 3.5 and 2.5 kD) obtained from Novel Experimental Technology, San Diego, Calif. The gel was stained with Coomassie Brilliant Blue R-250. The destained gel was scanned using a Personal Densitometer SI (Molecular Dynamics Inc., Sunnyvale, Calif.). The molecular weight of the purified protein, estimated using the FragmeNT Analysis software (version 1.1, Molecular Dynamics), was found to be approximately 74.9 kD based on the molecular weight standards.

Determination of Molecular Weight by MALDI-TOF Mass Spectral Analysis

Accurate measurement of the molecular weight of the 74 kD protein was carried out by Matrix Assisted Laser Desorption/Ionization Time-of-Flight (MALDI-TOF) mass spectrometry using a Lasermat™ 2000 linear mass analyzer (Finnigan Mat Limited). The Lasermat™ uses the technique of matrix-assisted laser desorption (35) to ionize the sample and Time of Flight to analyze the ions produced. The sample was embedded in a matrix of 3,5-dimethoxy-4-hydroxy-cinnamic acid (sinapinic acid) to enhance ionization of the sample. One microliter of the sample containing 5–10 pmol purified 74 kD protein was mixed with 1 µl of the matrix (10 mg/ml) dissolved in 70% (v/v) aqueous acetonitrile containing 0.1% (v/v) trifluoroacetic acid. One microliter of this sample and matrix mixture was loaded on a sample slide, allowed to dry and irradiated by a short pulse of UV light from a laser. Protein samples usually generate a relatively simple spectra in this method, since protein-related ions produced are predominantly of charge states z=+1 $[M+H]^+$ and z=+2 $[M+2H]^{2+}$. Bovine serum albumin (catalog no. A0281, Sigma Chemical Co., St. Louis, Mo.) of molecular weight 66,430.0 was used for external calibration.

The molecular weight of the 74 kD protein in the sample used for the SDS-PAGE analysis above was determined to be 73,987.7, while that of the 74 kD protein purified from *M. catarrhalis* TTA24 was 73,793.6. In addition to the expected $[M+H]^+$, the $[M+2H]^{2+}$ and the $[M+3H]^{3+}$ molecular ions of the 74 kD protein were also observed. Hence, it is reasonable to conclude that the molecular weight of the 74 kD protein is in fact approximately 74 kD, within the limits of experimental error.

Example 5

Amino Acid Composition Analysis

A sample of the 74 kD protein for amino acid analysis was hydrolyzed in glass tubes using 100 μl of 6 N HCl containing 5% phenol and 1% 2-mercaptoethanol under vacuum for 22 hours at 110° C. The samples were subsequently dried under vacuum followed by resolubilization in sample dilution buffer Na-S (Beckman Instruments, Inc., Fullerton, Calif., U.S.A.). The amino acid composition was determined on a Beckman model 6300 Amino Acid Analyzer (36) using a three step Na-citrate gradient according to manufacturer's instructions. The results were expressed as mol of residues per mol of the 74 kD protein based on a molecular weight of the 74 kD protein of 74,000. Cysteine and tryptophan residues were not determined. Threonine and serine residues were not corrected for destruction caused by the method of analysis used. Nine microliters of sample (purified from *M. catarrhalis* O35E—salt wash vesicles) were dried down and subjected to acid hydrolysis and subsequent amino acid analysis. Results reported in Table 2 represent the mean of duplicate determinations.

TABLE 2

Amino Acid Composition of the 74 kD Protein

| Amino acid | residues per mol |
|---|---|
| Asp + Asn | 104 |
| Thr | 58 |
| Ser | 44 |
| Glu + Gln | 67 |
| Pro | 27 |
| Gly | 77 |
| Ala | 56 |
| Val | 35 |
| Met | 6 |
| Ile | 21 |
| Leu | 40 |
| Tyr | 25 |
| Phe | 28 |
| His | 8 |
| Lys | 72 |
| Arg | 21 |

Example 6

Amino (N-) Terminal Amino Acid Sequence Analysis

Purified 74 kD protein preparations were subjected to SDS-PAGE (34) to determine homogeneity. Samples which contained traces of impurities were subsequently subjected to electrophoretic transfer onto a polyvinylidene difluoride membrane (ProBlott membrane, Applied Biosystems, Foster City, Calif.) using 10 mM 3-[cyclohexylamino]-1-propanesulfonic acid (CAPS), 10% methanol (pH 11.0) as the transfer buffer (37). The membrane was stained with Coomassie Brilliant Blue R-250 and the main band corresponding to the 74 kD protein was cut out. Amino-terminal protein sequence analysis was carried out using an Applied Biosystems Model 477A Protein/Peptide Sequencer equipped with an on-line Model 120A PTH Analyzer (Applied Biosystems). After the cleavage of each successive amino-terminus, the anilinothiazolinone derivative formed was converted to the more stable phenylthiohydantion (PTH) derivative by treatment with 25% trifluoroacetic acid at 64° C. for 20 minutes. The PTH derivatives were separated and identified on the PTH analyzer by reversed-phase HPLC using a Brownlee PTH C-18 column (particle size 5 μm, 2.1 mm i.d.×22 cm l.; Applied Biosystems) with a modified two solvent gradient system developed by the manufacturer (35). The following summarizes the results of N-terminal sequence analysis of different preparations of the 74 kD protein:

For the 74 kD protein purified from salt wash vesicles of *M. catarrhalis* O35E strain, approximately 18.7 μl of sample containing 20 μg of purified protein was subjected to SDS-PAGE followed by electroblotting and 20 cycles of N-terminal protein sequence analysis. The first 13 residues were determined except for an unidentified peak at residue 1 (SEQ ID NO:1):

```
Xaa Gly Gly Ser Gly Gly Ser Asn Pro Pro Ala Pro Thr
 1               5                   10
```

For the 74 kD protein purified from a whole cell extract of *M. catarrhalis* O35E strain, approximately 7.41 μl of sample containing 20 μg of purified protein was subjected to SDS-PAGE followed by electroblotting and 25 cycles of N-terminal protein sequence analysis. The first 17 residues were determined except for an unidentified peak at residue 1 (SEQ ID NO:2):

```
Xaa Gly Gly Ser Gly Gly Ser Asn Pro Pro Ala Pro
 1               5                   10
Thr Pro Ile Pro Asn
         15
```

For the 74 kD protein purified from a whole cell extract of *M. catarrhalis* TTA24 strain, approximately 14.3 μl of sample containing 74.4 μg of purified protein was directly loaded in the sequencer and 30 cycles of N-terminal protein sequence analysis performed. The first 20 residues were determined except for an unidentified peak at residue 1 (SEQ ID NO:3):

```
Xaa Gly Gly Ser Gly Gly Ser Asn Pro Pro Ala Pro
 1               5                   10
Thr Pro Ile Pro Asn Ala Ser Gly
         15                  20
```

The unidentified peak at residue 1 for each of the above samples was identical and followed the PTH-Glu peak by approximately 0.2 minutes.

Example 7

Extended N-Terminal Amino Acid Sequence Analysis

During N-terminal sequence analysis of the 74 kD protein, the abundance of proline (Pro) residues was recognized to cause early termination of the sequence read. Pro residues are partially released during the standard acid cleavage step in sequencing. Release of the remaining Pro with subsequent residues causes difficulty in sequence identification. In order to generate longer N-terminal sequences of the 74 kD protein, extended acid cleavage at Pro residues was carried out. This produced better results, but caused an increased amino acid background which seemed to be due to the simultaneous sequencing of acid induced non-specific cleavage products of the 74 kD protein. Chemical reduction of amino acid background build up during sequence analysis was carried out at some of the cycles where proline residues occurred. This was accomplished by introducing O-phthalaldehyde, a reagent which specifically reacts with amino groups of all N-terminal primary amino acids, without affecting corresponding prolyl residues, thereby blocking the residual protein/peptide chains (background) from subsequent sequencing (39,40). Twenty milligrams of O-phthalaldehyde were dissolved in 50 µl of 2-mercaptoethanol in 10 ml of acetonitrile and placed in the X1 bottle in the sequencer. Twenty-six microliters of the 74 kD protein (a lot purified from *M. catarrhalis* O35E—whole cell extract) containing 80.6 µg of protein was loaded on the sequencer. During sequencing, extended trifluoroacetic acid cleavage was carried out for Pro residues at 9, 10, 12, 14 and 16, whereas O-phthalaldehyde treatment was carried out for Pro residues at 9 and 16. This led to effective background reduction and resulted in extended N-terminal sequence determination (the first 27 residues) of the 74 kD protein (SEQ ID NO:4):

```
Xaa Gly Gly Ser Gly Gly Ser Asn Pro Pro Ala Pro
 1               5                   10
Thr Pro Ile Pro Asn Ala Ser Gly Ser Gly Asn Thr
           15                  20
Gly Asn Thr
   25
```

This sequence was analyzed using the BLAST alignment program to search for homology with other proteins. No significant homology was seen with any bacterial proteins in the previously listed data bases.

A similar procedure was used to obtain an N-terminal sequence for the 74 kD protein from *M. catarrhalis* 430–345 strain. One and one-half nmol of the 74 kD protein from *M. catarrhalis* 430–345 strain was subjected to N-terminal protein sequence analysis using an Applied Biosystems Model 477A Protein/Peptide Sequencer equipped with an on-line Model 120A PTH Analyzer (Applied Biosystems), as described above. During sequencing, extended trifluoroacetic acid cleavage was carried out for the Pro residue at 14, whereas O-phthalaldehyde treatment was carried out for Pro residues at 10 and 16. The first eighteen N-terminal residues were determined, again with the first residue not determined (SEQ ID NO:5):

```
Xaa Gly Gly Ser Gly Gly Ser Asn Pro Pro Ala Pro
 1               5                   10
Thr Pro Ile Pro Asn Ala
           15
```

Example 8
Amino Acid Sequence Analysis of Internal Peptides

A sample of the 74 kD protein (1.5 mg of a lot purified from *M. catarrhalis* O35E—whole cell extract) was digested overnight at 37° C. in PBS with chymotrypsin (Boehringer Mannheim Biochemicals, Indianapolis, Ind.) using a substrate:enzyme ratio of 1:60 (w/w). Digestion was complete as adjudged by SDS-PAGE analysis. The digest was purified by reversed phase HPLC using a Vydac Protein C4 column (particle size 5 µm, 0.46 cm i.d.×25 cm l; The Separations Group, Hesperia, Calif.). The HPLC conditions were as follows: flow rate 1.0 ml/min; Solvent A=0.1% aqueous trifluoroacetic acid; Solvent B=acetonitrile: water, 80:20 (v/v) containing 0.1% (v/v) trifluoroacetic acid; linear gradient of 0–100% Solvent B over 45 minutes. Eluted peaks were detected by their absorbance at 220 nm and fractions were collected. The fractions were dried down and each resuspended in 50 µl water. Suitable fractions were pooled and aliquots were subjected to Tricine-SDS-PAGE (41) using 10–18% (v/v, acrylamide) gradient gels. The gels were stained with Coomassie Brilliant Blue R-250 followed by transfer on to polyvinylidene difluoride membrane as stated above. Four different bands were cut out and subjected to N-terminal amino acid sequence analysis. Two of the peptides, 'fragment 1' (SEQ ID NO:6) and 'fragment 3' (SEQ ID NO:8), generated essentially identical 14-residue sequences; the only difference was that the N-terminal residue was Thr for the former, while Gly was the predominant corresponding residue for the latter, although a lower amount of Thr could be detected. Both of these sequences overlapped over four residues with the N-terminal sequence of another peptide 'fragment 2' (SEQ ID NO:7) to generate a continuous stretch of 25 amino acid residues. Since chymotrypsin usually cleaves proteins on the carboxy terminal side of Trp, Tyr, Phe, Leu and Met residues, it is evident that partial cleavage of the $Tyr^{10}$-$Asn^{11}$ bond in either of the peptides 'fragment 1' or 'fragment 3' gave rise to the peptide 'fragment 2'. On the other hand, partial cleavage of the $Tyr^4$-$Gly^5$ bond in 'fragment 2' permitted sequence information beyond this point to be obtained. Also, it was evident that both of the peptides 'fragment 1' and 'fragment 3' were sequenced in their entirety.

```
Thr Asp Glu Lys Asn Lys Pro Asp Gly Tyr Asn Gly Glu Tyr
 1               5                   10
(Fragment 1; SEQ ID NO:6)

Asn Gly Glu Tyr Gly His Ser Ser Glu Phe Thr Val Asn Phe Lys
                     1               5                   10                  15
                              (Fragment 2; SEQ ID NO:7)

Gly Asp Glu Lys Asn Lys Pro Asp Gly Tyr Asn Gly Glu Tyr
(Thr)
 1               5                   10
(Fragment 3; SEQ ID NO:8)

|--------------------------------25-------------------------------------------------|
```

In addition to the above, a fourth chymotryptic peptide ('fragment 4' (SEQ ID NO:9)) gave the following sequence over twenty of its N-terminal residues. The Thr at residue 20 could not be assigned with certainty.

```
Lys Ser Ile Val Ile Arg Asp Ala Asp Val Thr Gly
 1               5                       10
Gly Phe Tyr Tyr Pro Asn Ala (Thr)
           15                  20
(Fragment 4; SEQ ID NO:9)
```

These sequences were analyzed using the BLAST alignment program for comparison with other proteins in the previously listed data bases. The 25 amino acid peptide generated by the overlap of the fragments 1 through 3 had homology with a conserved portion of the TbpB protein from *Neisseria meningitidis*, as well as with a similar sequence from *Haemophilus influenzae*. Fragment 4 was found to have homology with a repeated sequence in the TbpB protein from *Neisseria meningitidis*.

Example 9

Bactericidal Activity of Antiserum to the 74 kD Protein

A bactericidal assay was performed as described previously (11). Briefly, 50 µl of bacterial suspension (approximately 1,200 colony forming units (CFUs) in PBS containing 1 mM $CaCl_2$ and 0.2 mM $MgCl_2$) were mixed, and incubated with 25 µl of antiserum against the 74 kD protein (same as used in Table 1) for 30 minutes at 4° C. Antiserum was tested at 3-fold dilutions starting from 1:50. Twenty-five µl of immunoglobulin-depleted human serum was then added as the complement source, and the mixture incubated an additional 30 minutes at 35° C. The number of remaining viable bacteria was determined by plating 50 µl of the assay mixture on Mueller-Hinton agar plates. The control consisted of bacteria, test sera and complement serum which had been heat-inactivated at 55° C. for 30 minutes. Whole cell ELISA and bacteridal titers were determined based on pooled serum samples. The percentage of bacteria killed was calculated by the following formula: % killing= 100×(CFU from the control—CFU from the sample)/CFU from the control). The bactericidal activity of the antisera was expressed as bactericidal titer, i.e., the highest serum dilution resulting in killing of 50% or more of the bacteria.

The mouse antisera raised against the 74 kD proteins in several studies were tested in a bactericidal assay against seven *M. catarrhalis* strains. BALB/c mice (10 animals/group, female, 6–8 week old at the beginning of the study) were immunized at weeks 0 and 4 with 1 µg of antigens mixed with 25 µg of Stimulon™ QS-21. The results are presented in Table 3:

TABLE 3

Bactericidal (BC) activity of the anti-74 kD sera

| Assay strain | BC titer of week 6 sera to 74 kD protein from strain | | | | |
|---|---|---|---|---|---|
| | O35E | | | 430-345 | |
| | Study 1 | Study 2 | Study 3 | Study 2* | Study 3 |
| O35E | <50 | <50 | <50 | 450 | <50 |
| TTA24 | 400 | 50 | 50 | 150 | 150 |
| 430-345 | ND** | 4,050 | 4,050 | 4,050 | 12,150 |
| ATCC25238 | 400 | 150 | 50 | 450 | <50 |
| 125-114 | 1000 | 150 | 150 | 1,350 | 450 |
| 216-96 | 1000 | 50 | 150 | 1,350 | 150 |
| 1230-359 | <50 | 450 | ND | 1,350 | ND |

*Strain 430-345 was not tested in Study 1.
**ND = not done.

Sera against the 74 kD protein purified from strains O35E or 430-345 exhibited killing of almost all strains (Table 3). The O35E strain appears to be resistant to bactericidal effects elicited by the 74 kD protein of that strain. The bactericidal titers varied from strain to strain and appeared to correlate with whole-cell ELISA titers (data not shown). For almost every strain assayed, the bactericidal titers were higher for the antiserum against the 74 kD protein from strain 430-345 than that against the O35E strain. This is consistent with whole cell-ELISA titers. Pre-immune sera from the same animals were not bactericidal.

Thus, antibodies to the 74 kD protein consistently exhibited bactericidal activities against heterologous strains of *M. catarrhalis* in spite of low antibody titers by whole cell ELISA. This suggests that the bactericidal antibodies are directed toward the conserved epitopes of the 74 kD protein.

Antibodies against the 74 kD protein from strain TTA24 were bactericidal towards all six strains assayed and the titers were >500. These results are presented in Table 4:

TABLE 4

Bactericidal titers of the week 6 serum from mice immunized with 74 kD protein from TTA24 strain or with a mixture of 74 kD protein from TTA24 and 430-345 strains

| Assay strain | Antisera to 74 kD Protein from Strains | |
|---|---|---|
| | TTA24 | TTA24 + 430-345 |
| O35E | 1,163 | 948 |
| TTA24 | >6,400 | >6,400 |
| 125-114 | 1,011 | 1,452 |
| 430-345 | 1,303 | >12,800 |
| 216-96 | 587 | 326 |
| 1230-359 | 555 | 1,181 |

Antisera to the mixture of 74 kD proteins from strains TTA24 and 430-345 exhibited equivalent bactericidal titers against the heterologous strains.

Example 10

Effect of Adjuvants on Whole Cell ELISA Titers

Several adjuvants were compared to determine if the selection of adjuvant might augment the antibody response to the conserved epitopes of the 74 kD protein from O35E strain. Sera generated against 74 kD protein from O35E strain were assayed against seven strains of *M. catarrhalis* by whole cell ELISA. In this assay, BALB/c mice (10 animals/group, female, 6–8 week old at the beginning of the study) were immunized at weeks 0 and 4 with 1 µg of 74 kD protein. The doses of adjuvants were: 25 µg for Stimulon™ QS-21, 50 µg for MPL™, and 100 µg for aluminum phosphate (alum). Immune sera were made with proteins purified from O35E strain. Whole cell ELISA titers were determined on pooled week 6 sera. The results are shown in Table 5:

TABLE 5

Reactivity of the antibodies elicited by 74 kD protein using different adjuvants

| | whole cell ELISA titer to *M. catarrhalis* strain | | | | | | |
|---|---|---|---|---|---|---|---|
| adjuvant | O35E | 430:345 | TTA24 | ATCC | 125-114 | 216-96 | 1230 |
| saline | 102,274 | 17,023 | 195 | 160 | 2,271 | 270 | 1,091 |
| QS-21 | 1,910,012 | 789,405 | 1,058 | 1,083 | 18,368 | 5,313 | 6,061 |
| MPL | 1,193,747 | 213,435 | 349 | 769 | 1,255 | 122 | 1,639 |
| Alum | 235,736 | 33,117 | 484 | 300 | 1,488 | 2,643 | 1,185 |
| MPL + Alum | 2,443,332 | 138,246 | 5,380 | 6,292 | 14,889 | 11,205 | 4,283 |

Based on titers to the homologous strain, it appeared that the adjuvants Stimulon™ QS-21, MPL™ and the MPL™-alum mixture all potentiated the immunogenicity of the 74 kD protein to a similar degree, while aluminum phosphate did not appear to act as an adjuvant. When whole cell ELISA titers against heterologous strains were examined, only 74 kD protein adjuvanted with Stimulon™ QS-21 or MPL™-alum elicited significant titers of antibodies. Mice immunized with 74 kD protein and MPL™ appeared to have much lower titers of antibodies which were equivalent to those from the non-adjuvanted group.

Example 11

Effect of Adjuvants on Bactericidal Activity

Bactericidal antibody titers were assayed with sera generated against 74 kD protein from O35E strain using different adjuvants. The results are shown in Table 6:

TABLE 6

The bactericidal activity of the antibodies elicited by 74 kD protein using different adjuvants

| | BC titers assayed against | | | | | |
|---|---|---|---|---|---|---|
| adjuvant | O35E | 430:345 | TTA24 | 125-114 | 216-96 | 1230 |
| saline | <100 | 891 | <100 | <100 | <100 | <100 |
| QS-21 | <100 | >6,400 | 147 | 374 | 180 | 500 |
| MPL | <100 | <100 | <100 | <100 | <100 | 113 |
| Alum | <100 | <100 | <100 | <100 | <100 | <100 |
| MPL + Alum | <100 | 443 | 151 | 354 | 216 | 275 |

Only sera generated to 74 kD protein using Stimulon™ QS-21 or the mixed adjuvant exhibited bactericidal activity towards heterologous strains. Thus, Stimulon™ QS-21 and the mixed adjuvants appeared to augment antibody response to the conserved epitopes of the 74 kD protein.

Example 12

Immunogenicity Of The Purified 74 kD Protein

Female BALB/c mice (Taconic Farms, Germantown, N.Y.), age 6–8 weeks, were immunized subcutaneously on weeks 0 and 4 with 1 μg of purified 74 kD protein formulated with 25 μg of the adjuvant Stimulon™QS-21 unless otherwise stated. Control mice were injected with 1 μg of $CPM_{197}$ (a non-toxic variant of diphtheria toxin) and Stimulon™ QS-21. Serum samples were collected at weeks 0 and 6. Mice were challenged intratracheally with $3.5 \times 10^5$ CFUs of bacteria five days after the final bleed at week 7.

The immunogenicity of the purified 74 kD protein was evaluated in these mice in several studies which gave similar results. A representative study is shown in Table 7. ELISA titers were determined on pooled serum samples from ten mice using purified protein as the detection antigen. As shown in Table 7 below, the purified 74 kD protein was immunogenic in mice. Immunization with two 1 μg doses of antigen four weeks apart elicited high antibody titers toward the purified protein by ELISA (Table 7). Antibodies elicited by the 74 kD antigen purified from either O35E or 430-345 strains reacted strongly against the purified 74 kD antigen from both strains, suggesting that 74 kD proteins from these two strains were antigenically similar. When these sera were tested against purified 74 kD protein from TTA24 strain by ELISA, low titers were detected (Table 7). Thus, the 74 kD protein from TTA24 strain appears to differ antigenically from the 74 kD proteins of strains O35E or 430-345. However, when antibodies made against 74 kD protein from TTA24 strain were assayed against the protein from O35E strain, a moderate titer was detected. This suggested that there is some conservation between 74 kD proteins from TTA24 and O35E strain, and the strain specific epitopes may be more immunogenic than conserved epitopes in 74 kD protein of the O35E strain. The antisera did not react with other *M. catarrhalis* proteins tested, namely recombinant CopB, recombinant C/D, or purified UspA, as tested by ELISA or western blot (data not shown).

TABLE 7

Immunogenicity of the 74 kD Protein from Various Strains

| 74 kD protein from strain | Week 6 serum IgG titer elicited by 74 kD protein from strain | | |
|---|---|---|---|
| | O35E | 430-345 | TTA24 |
| O35E | 714,085 | 952,314 | 10,580 |
| TTA24 | 144 | 520 | 6,856,399 |
| 430-345 | 364,620 | 2,328,895 | ND |

Figure 5:
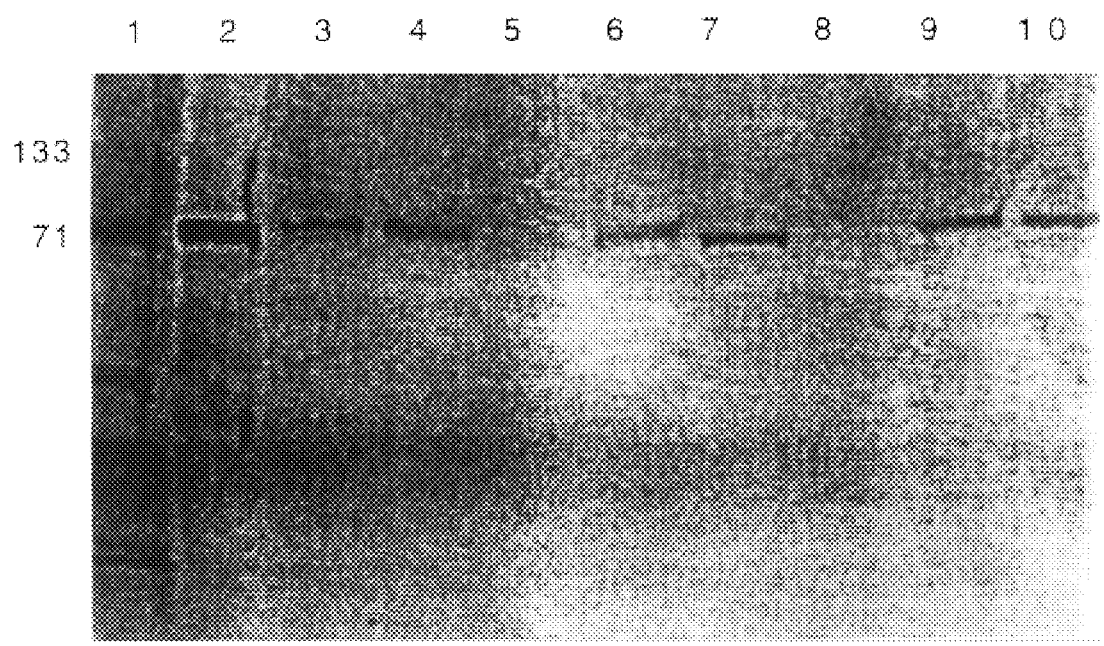
FIG. 5 depicts the reactivity of the mouse anti-74 kD serum to heterologous strains of *M. catarrhalis*. Bacterial lysates containing 10 μg of total protein were resolved in 4–15% SDS-PAGE and tested in a western blot with mouse antiserum against the purified 74 kD protein from O35E strain (1:5,000). Lanes 2–10 are strains O35E, TTA24, ATCC25238, 324-171, 128–179, 430-345, 111-210, 219-96, and 1230-359, respectively. The molecular weight standards (lane 1) are 133 kD (β-galactosidase) and 71 kD (bovine serum albumin).

The antisera raised against 74 kD proteins from strains O35E and 430-345 in mice were tested in a whole cell ELISA against several *M. catarrhalis* strains. Doses in columns 1, 3 and 5 of Table 8 below were 2×1 μg protein; doses in columns 2 and 4 were 2×5 μg protein. The adjuvant used was 25 μl of Stimulon™ QS-21. These sera exhibited high whole-cell ELISA titers against O35E and 430-345 strains, but titers to 5 other strains were much lower (Table 8). When whole cell lysates from nine *M. catarrhalis* strains were resolved by 4–15% SDS-PAGE, blotted onto nitrocellulose membrane and probed with antiserum against the 74 kD protein, only a single band at the 74 kD region was detected for all the isolates (see FIG. 5). This indicated that the titers toward whole bacteria cells were due to specific reactivity to the 74 kD protein.

TABLE 8

Immunogenicity of the 74 kD Protein from
Strains O35E and 430-345:
IgG titers by whole cell ELISA

| Assay | Mouse antisera to 74 kD protein from Strain | | | | |
|---|---|---|---|---|---|
| strain | O35E | O35E | O35E | 430-345 | 430-345 |
| O35E | 407,052 | 615,078 | 443,282 | 1,155,447 | 2,338,191 |
| 430-345 | 145,084 | 160,387 | 170,075 | 724,369 | 591,861 |
| TTA24 | 3,458 | 203 | 532 | 711 | 2,105 |
| ATCC25238 | 7,203 | 618 | 659 | 2,542 | 2,028 |
| 125-114 | 3,990 | 174 | 899 | 4,488 | 3,042 |
| 216-96 | 7,163 | 593 | 394 | 3,518 | 12,576 |
| 1230-359 | 7,417 | 4,609 | 2,726 | 5,518 | 4,390 |

74 kD Protein from TTA24 Strain: It is clear that the 74 kD proteins from strains O35E and 430-345 are antigenically similar. Antibodies elicited by 74 kD protein from these two strains reacted poorly to many other strains of the *M. catarrhalis*, including TTA24 strain. Because of this observation, the 74 kD protein from the TTA24 strain was purified and evaluated in mice to determine whether it exhibited a similar pattern of conservation. As part of this experiment, a mixture of the two antigenically different 74 kD proteins was also examined.

BALB/c mice (10 animals/group, female, 6–8 week old at the beginning of the study) were immunized at weeks 0 and 4 with 5 μg of 74 kD protein (10 μg for the mixed 74 kD group) mixed with 25 μg of Stimulon™ QS-21. Whole cell ELISA titers were determined on pooled serum samples. Sera against 74 kD from O35E strain from a previous study was included as reference in the assay. The results are shown in Table 9:

TABLE 9

The immunogenicity of the 74 kD protein from TTA24
strain and antibody reactivity to heterologous strains

| | IgG titer of the sera made against 74 kD from strain | | |
|---|---|---|---|
| Assay strain | TTA24 | TTA24 + 430-345 | O35E |
| O35E | 26,448 | 568,446 | 958,469 |
| 430-345 | 51,460 | 731,124 | 376,289 |
| 1230-359 | 28,470 | 68,757 | 59,666 |
| TTA24 | 1,832,305 | 1,386,747 | 659 |
| 125-114 | 44,838 | 24,971 | 777 |
| 216-96 | 97,751 | 86,375 | 4,202 |
| ATCC25238 | 55,873 | 56,031 | 6,159 |
| 111-210 | 52,369 | 85,800 | 2,708 |
| 301-221 | 246,416 | 156,427 | 369 |
| 205-221 | 10,025 | 6,272 | 598 |
| 324-171 | 300,613 | 154,140 | 655 |

Figure 6:
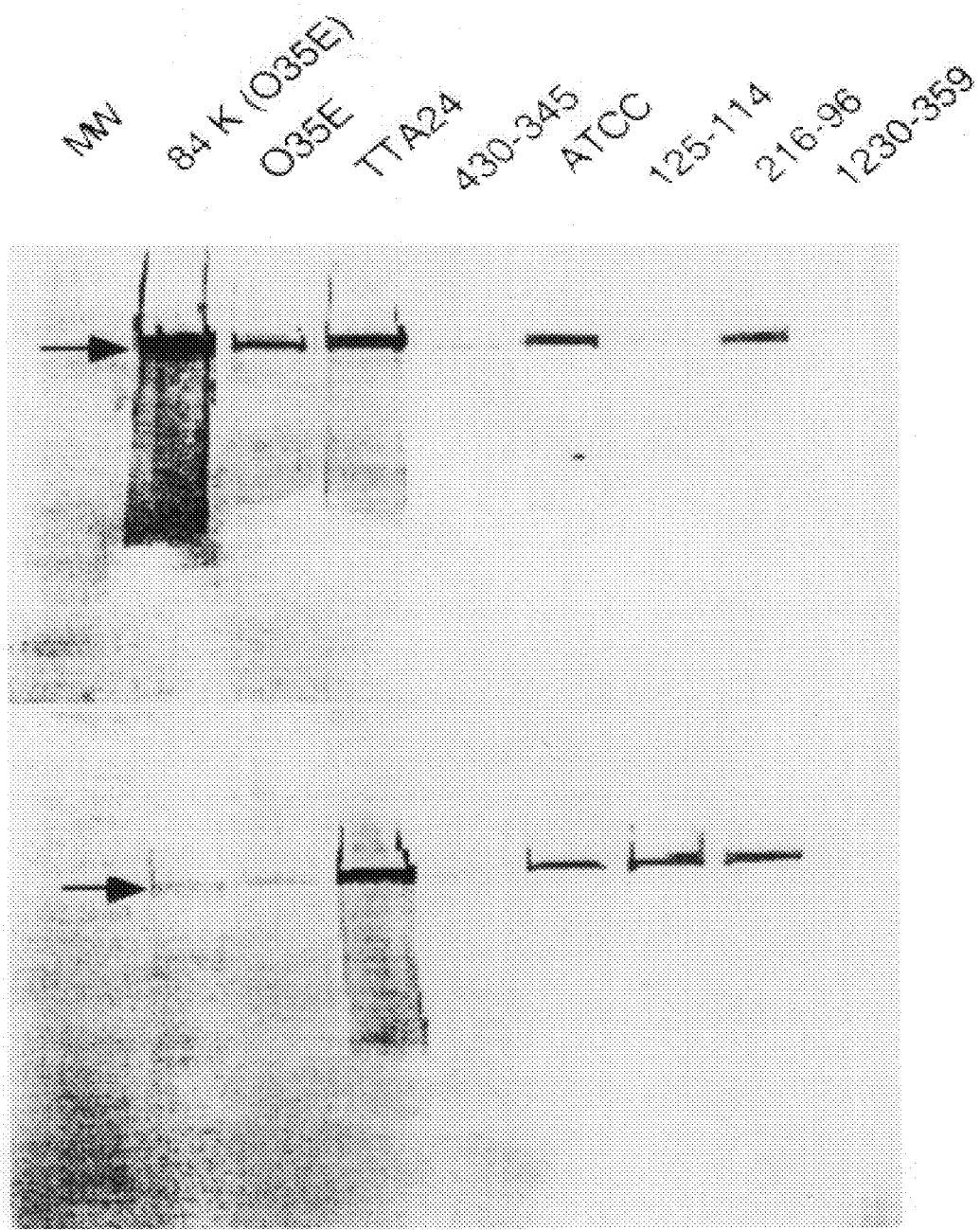
FIG. 6 depicts the Western blot analysis of mouse antisera raised against the 74 kD protein from TTA24 strain (bottom) or pooled 74 kD proteins from strains TTA24 and 430-345 (top). Each lane was loaded with 10 μg of whole bacterial lysates or 1.5 μg of purified 74 kD protein. Antisera were from week 6 bleeding diluted 1:1,000.

The results from Table 9 indicated that antibodies elicited by 74 kD protein from TTA24 strain exhibited very high titer against the homologous strain and moderately high titers against 10 heterologous strains by whole cell ELISA. Titers against heterologous strains are significantly higher than those of sera elicited by 74 kD proteins from strains O35E and 430-345. Specific reactivity of the serum to the 74 kD protein was confirmed by western blot (FIG. 6 bottom).

As expected, a pool of 74 kD proteins from strains TTA24 and 430-345 elicited a high level of antibodies against the homologous strains and the antigenically related strain O35E. Both the ELISA and bactericidal antibody titers against eight other strains were nearly the same as the titers elicited by 74 kD protein from TTA24 strain alone (Table 9). Specific reactivity of the antibody to the 74 kD protein was confirmed by western blot (FIG. 6 top).

In summary, the 74 kD protein from *M. catarrhalis* strains appears to exhibit antigenic variation. The TTA24 strain appears to express a form of the 74 kD protein that is better conserved than those of strains O35E and 430-345. The 74 kD protein from TTA24 strain elicited antibodies reactive to all strains of *M. catarrhalis* assayed. It also appeared unnecessary to use a mixture of the 74 kD proteins to generate a good response.

Example 13

Enhanced Pulmonary Clearance of *M. catarrhalis* in Mice

To determine if immunization with purified 74 kD protein would enhance pulmonary clearance of intratracheally deposited bacteria in a murine model, mice immunized with the 74 kD protein prepared from strains O35E and 430-345 were challenged with O35E or TTA24 strains of *M. catarrhalis*. The challenge was performed using a procedure previously described (11). In summary, $3.5 \times 10^5$ CFUs of bacteria from a mid-logarithmic culture were instilled intratracheally into the lungs of anesthetized mice by intramuscular injection of a mixture of 2 mg of ketamine HCl (Fort Dodge Lab., Ford Dodge, Iowa) and 0.2 mg of acepromazine maleate (Butler Co., Columbus, Ohio). Viable bacteria were recovered from the mouse lungs six hours after challenge, and the percentage of bacterial clearance in immunized mice was determined relative to the CFUs recovered from the control animals. Control animals were immunized with $CRM_{197}$ and Stimulon™ QS-21. Statistical analysis was performed using the Wilcoxon rank sum test (JMP Software, SAS Institute, Cary, N.C.). A probability (p) value of less than 0.05 was considered statistically significant.

Eight groups of mice in several studies which were immunized with purified 74 kD protein from the O35E strain were challenged with either the O35E or the TTA24 strains. Groups 9 and 10 were immunized with 74 kD protein from 430-345 strain and challenged with either O35E strain (group 9) or TTA24 strain (group 10). BALB/c mice (female, 6–8 weeks old at the beginning of the study, 10 per group) were immunized at weeks 0 and 4 with 1 μg of antigens mixed with 25 μg of Stimulon™ QS-21. Sera, collected 4 days before challenge, were assayed against the challenge strain by whole cell ELISA. Results are expressed as IgG endpoint titers on pooled samples. The $CRM_{197}$ control had ELISA titers of less than 100 in the same assay. Mice were challenged intratracheally with $3.5 \times 10^5$ CFUs of bacteria and viable bacteria recovered from the lungs 6 hours after challenge. The percent clearance is the percentage of bacteria cleared from the immunized mice compared to control which were immunized with $CRM_{197}$ and Stimulon™ QS-21. The results of the pulmonary clearance study are shown in Table 10:

TABLE 10

Pulmonary clearance of *M. catarrhalis* in a murine challenge model after active immunization

| Group | 74 kD source | Challenge strain | ELISA titer | % clearance | p value |
|---|---|---|---|---|---|
| 1 | O35E | O35E | 407,000 | 68 | 0.0002 |
| 2 | O35E | O35E | 168,000 | 70 | 0.0006 |
| 3 | O35E | O35E | 102,274 | 63 | 0.0025 |
| 4 | O35E | O35E | 1,910,012 | 52 | 0.0004 |
| 5 | O35E | O35E | 1,193,747 | 57 | 0.0114 |
| 6 | O35E | O35E | 235,736 | 47 | 0.0047 |
| 7 | O35E | O35E | 2443,332 | 56 | 0.0003 |
| 8 | O35E | TTA24 | 140 | −35 | 0.15 |
| 9 | 430-345 | O35E | 627,148 | 49 | 0.0043 |
| 10 | 430-345 | TTA24 | 337 | −11 | 0.41 |
| 11 | TTA24 | O35E | 26,341 | 29 | 0.318 |
| 12 | TTA24 | TTA24 | 673,754 | 76 | 0.009 |

The bacterial clearance relative to control for each experiment was considered statistically significant by the Wilcoxon signed rank test if p was less than 0.05.

Relative to control mice immunized with $CRM_{197}$, enhanced pulmonary clearance of heterologous bacteria was only seen for the mice challenged with O35E strain (Table 10). The lack of enhanced clearance of TTA24 was consistent with the poor antibody reactivity toward this strain in the whole-cell ELISA (see Table 8). Enhanced clearance of O35E, but not TTA24 strain, was also seen in mice immunized with purified 74 kD protein from strain 430-345 (Table 10). Again this correlated with the whole cell reactivity of the antibodies. The 74 kD protein from TTA24 appears to be antigenically different from that of the O35E or 430-345 strain. This may account for the inability of mice immunized with the 74 kD proteins to clear this strain. Animal challenge data suggest that immunization with purified 74 kD protein will induce enhanced pulmonary clearance of *M. catarrhalis* strains bearing antigenically similar 74 kD proteins.

Example 14

Detection of Human Serum Antibodies to the 74 kD Protein

Studies indicated that healthy adult sera contain naturally acquired antibodies specific for *M. catarrhalis* (data not shown). To determine if they were directed toward the 74 kD protein, sera from six healthy adults were assayed for reactivity with the purified 74 kD protein from strains O35E and TTA24 by ELISA. All six sera had detectable titers, and titers to 74 kD protein of the TTA24 strain were higher as shown in Table 11:

TABLE 11

Normal human sera contain naturally acquired antibodies to the 74 kD protein

| | ELISA IgG titers to | |
|---|---|---|
| Human serum | 74 kD (O35E) | 74 kD (TTA24) |
| 1 (H92-X) | 213 | 2,928 |
| 2 (H89-M) | 591 | 10,148 |
| 3 (H89-L) | 1,203 | 5,944 |
| 4 (H89-D) | 1,053 | 5,932 |
| 5 (Kacu) | 1,361 | 9,415 |
| 6 (Kconv) | 4,683 | 21,592 |

Figure 7:
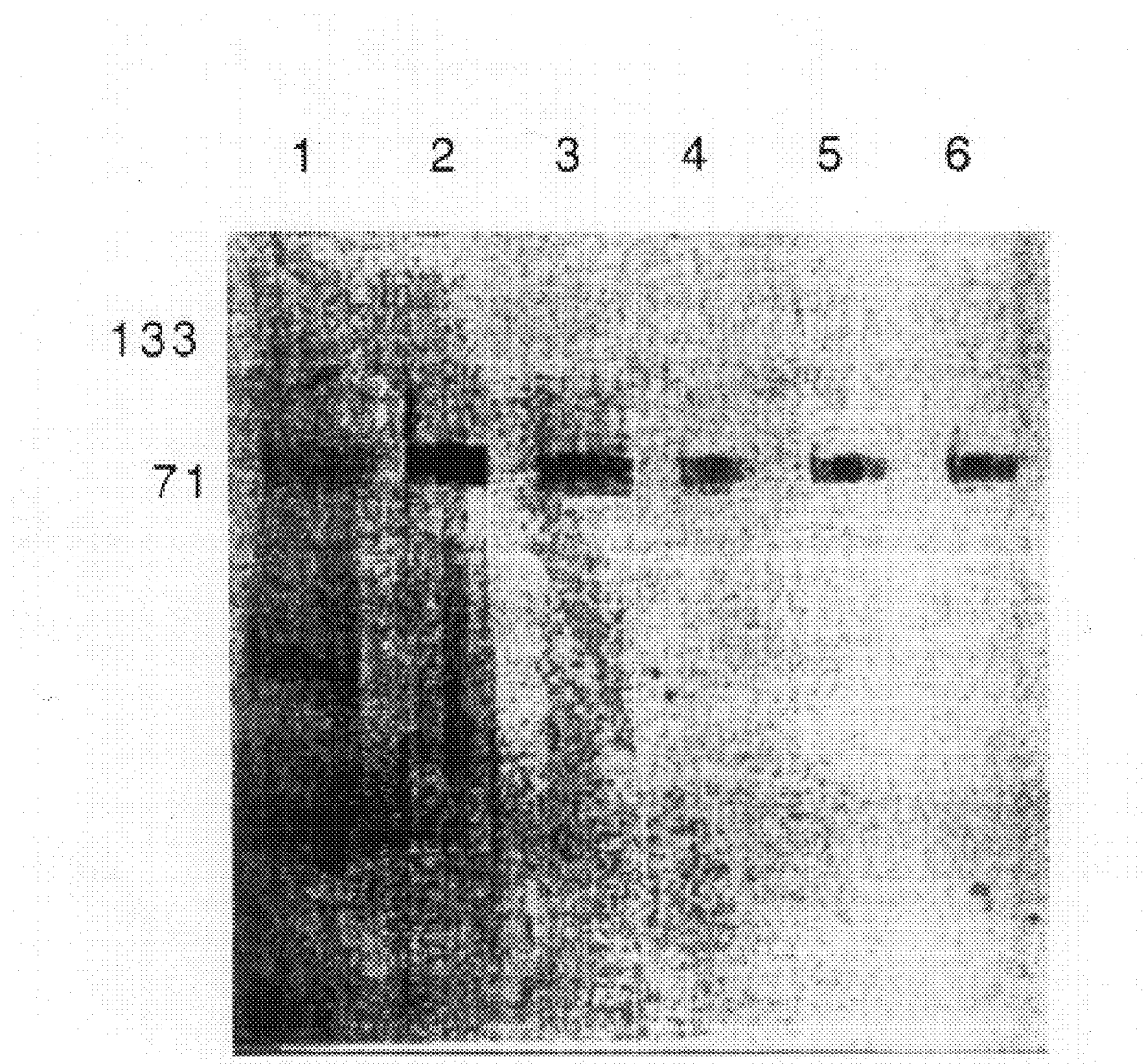
FIG. 7 depicts the presence of antibodies to the 74 kD protein in normal human sera. Purified 74 kD protein from O35E strain was reacted with five serum samples (Lanes 2–6) from healthy adults in a western blot. The molecular weight standards shown in lane 1 are the same as those described in FIG. 5.

Specific reactivity to the 74 kD protein was seen for every serum on western blot (see FIG. 7). This indicated that the 74 kD protein is expressed by the *M. catarrhalis* in vivo and is a target of the antibody response.

Example 15

Purification of 74 kD Specific Antibodies From Human Plasma

To determine if human antibodies to the 74 kD protein recognize epitopes on the bacterial surface, 74 kD specific antibodies from the pooled plasma of two healthy adults (American Red Cross, Rochester, N.Y.) were affinity purified. The antibodies were precipitated by adding ammonium sulfate to 50% saturation, resuspended and dialyzed against PBS. A nitrocellulose membrane (2×3 inches) was incubated with purified 74 kD protein from O35E strain at 1.0 mg/ml in PBS for one hour at RT, washed twice with PBS and residual binding sites on the membrane blocked with 5% (wt/vol) dry milk in PBS for two hours at RT. The membrane was then washed twice with PBS, 100 mM glycine (pH 2.5) and finally with PBS before incubation with the dialyzed antibody preparation. After incubating four hours at 4° C., the membrane was washed with PBS, and then 10 mM tris buffer (pH 8.0) containing 1 M sodium chloride to remove non-specifically bound proteins. The bound antibodies were eluted by incubating the membrane in 5 ml of 100 mM glycine (pH 2.5) for two minutes with shaking. One ml of tris-HCl (1M, pH 8.0) was immediately added to the eluate to neutralize the pH. The eluted antibodies were dialyzed against PBS, aliquoted, and stored at −20° C.

Figure 8:
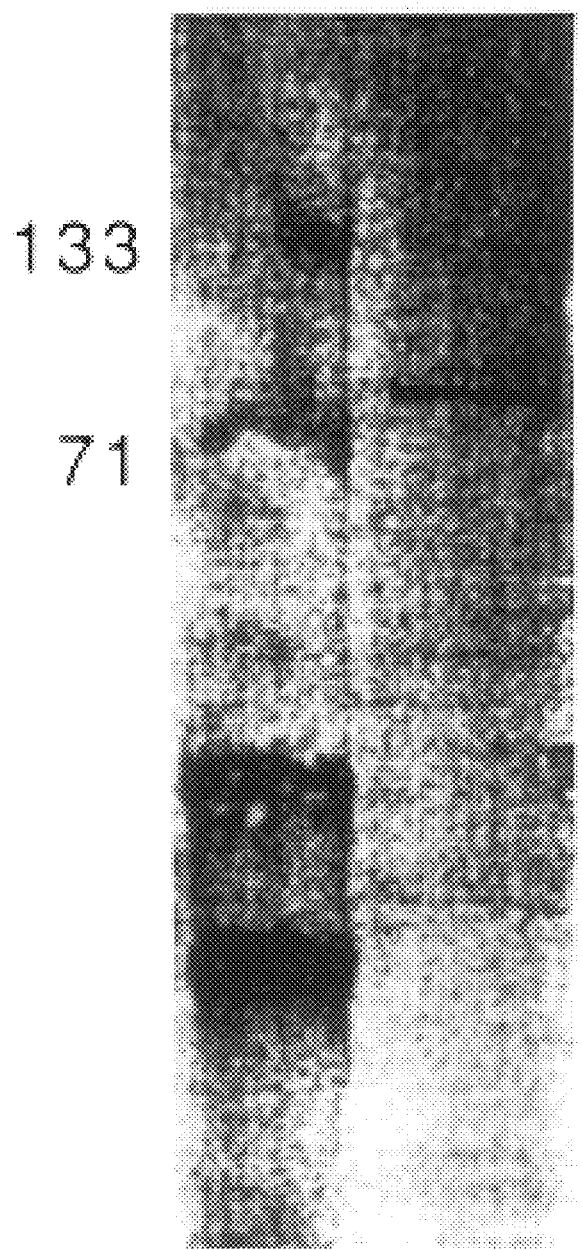
FIG. 8 depicts the reactivity of anti-74 kD protein antibodies purified from adult serum to the whole bacterial lysates. O35E strain lysates containing 10 μg of protein were reacted with affinity purified human antibodies against the 74 kD protein in a western blot (lane 2). The molecular weight standards shown in lane 1 are the same as those described in FIG. 5.

As shown in FIG. 8, a western blot confirmed that the purified antibody reacted specifically with the 74 kD protein, but did not react with the other outer membrane proteins from the whole cell lysates of O35E strain.

ELISA end point titers are the highest antibody dilutions giving an $A_{415}$ greater than three times the background when assayed against whole bacterial cells. As shown in Table 12, although the antibodies were prepared using the 74 kD protein from O35E strain and TTA24 strain, each reacted with five other strains by whole cell ELISA with similar titers:

TABLE 12

The whole cell reactivity of the 74 kD protein-specific antibodies purified from adult human plasma

| Assay Strain | IgG Titers of Antibodies Purified Using | |
|---|---|---|
| | O35E | TTA24 |
| O35E | 4,420 | 1,580 |
| TTA24 | 504 | 1,164 |
| ATCC25238 | 1,325 | 2,230 |
| 125:114 | 3,015 | 2,130 |
| 216:96 | 2,859 | 1,155 |
| 1230-359 | 1,960 | 822 |

The results shown in Table 12 indicated that humans mount an antibody response to the conserved surface epitopes of the 74 kD protein after natural infection.

Example 16

Inhibition of Transferrin Binding

Figure 9:
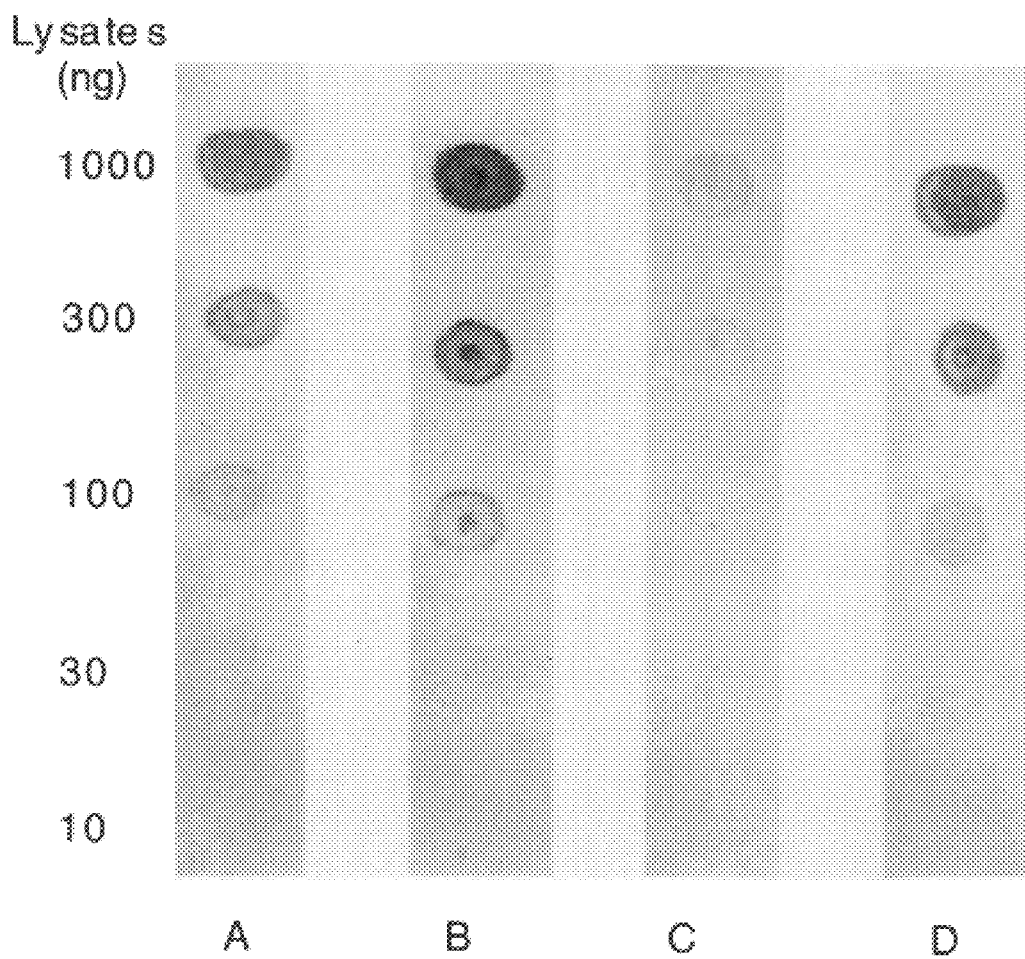
FIG. 9 depicts the inhibition of transferrin binding by antibodies to the 74 kD protein. Various amounts of O35E lysate were spotted on a nitrocellulose membrane. The membrane was incubated with PBS (panel A); 1:100 diluted normal mouse serum (panel B); anti-serum to the 74 kDa protein from O35E strain (panel C); or control anti-serum to the UspA (panel D). The membranes were then probed with biotin-labeled transferrin.

Because transferrin may be an in vivo iron source for *M. catarrhalis*, the binding of antibodies to the 74 kD protein on the bacterial surface may interrupt the iron acquisition process. Dot blotting was used to determine whether antibodies against the 74 kD protein could inhibit transferrin binding to the bacterial lysate. Three microliters of O35E lysate were applied to a nitrocellulose membrane. The membrane was blocked with PBS containing 5% dry milk, followed by incubation with mouse anti-serum (1:100 diluted in PBS containing 5% dry milk) to the 74 kD protein from O35E strain for two hours at room temperature. Normal mouse serum and mouse anti-serum to UspA were included as controls. The membrane was then sequentially incubated with biotin labeled transferrin, streptavidin-alkaline phosphatase and the enzyme substrate as described above. As depicted in FIG. 9, a reduction in transferrin binding was observed with antibodies to the 74 kD protein. In contrast, neither a normal mouse serum nor anti-UspA serum interfered with transferrin binding. This suggested that antibodies to the 74 kD protein specifically inhibit transferrin binding.

BIBLIOGRAPHY

1. Bluestone, C. D., et al., *Pediatr. Infect. Dis. J.*, 11. S7–S11 (1992).
2. Ruuskanen, O., and Heikkinen, T., *Pediatr. Infect. Dis. J.*, 13, S23–S26 (1994).
3. Shurin, P. A., et al., *Pediatr. Infect. Dis. J.*, 2, 34–38 (1983).
4. Van-Hare, G. F., et al., *Rev. Infect. Dis.*, 9, 16–27 (1987).
5. Boyle, F. M., et al., *Med. J. Aust.*, 154, 592–596 (1991).
6. Catlin, B. W., *Clin. Micro. Rev.*, 3, 293–320 (1990).
7. Jousimies-Somer, H. R., et al., *J. Clin. Microbiol.*, 27, 2736–2743 (1989).
8. Fung, C. P., et al., *J. Antimicrob. Chemother.*, 30, 47–55 (1992).
9. Fung, C. P., et al., *J. Antimicrob. Chemother.*, 33, 215–222 (1994).
10. Chen, D., et al., Antibodies to the UspA outer membrane protein of *Moraxella catarrhalis* block bacterial attachment in vitro and are protective in a murine pulmonary challenge model, *Abstracts of the 95th General Meeting of the American Society for Microbiology* 1995 (American Society for Microbiology, Washington, D.C. (1995)).
11. Chen, D., et al., *Infect. Immun.*, 64, 1900–1905 (1996).
12. Helminen, M. E., et al., *Infect Immun*, 61, 2003–10. (1993).
13. Helminen, M. E., et al., *J. Infect. Dis.*, 170, 867–872 (1994).
14. Christensen, J. J., et al., *Clinical and Diagnostic Laboratory Immunology*, 2, 14–17 (1995).
15. Faden, H., et al., *Ann. Otol. Rhinol. Laryngol.*, 103, 522–524 (1994).
16. Goldblatt, D., et al., *J. Infect. Dis.*, 162, 1128–1135 (1990).
17. Helminen, M. E., et al., *Clinical and Diagnostic Laboratory Immunology*, 2, 43–39 (1995).
18. Sethi, S., et al., *Infect. Immun.*, 63, 1516–1520 (1995).
19. Bonnah, R. A., et al., *Microb Pathog.*, 19, 285–297 (1995).
20. Altschul, S. F., et al., *J. Mol. Biol.*, 215, 403–410 (1990).
21. Bartos, L. C., and Murphy, T. F., *J. Infect. Dis.* 158, 761–765 (1988).
22. Aebi, C., et al., *Infect. Immun.*, 64, 2024–2030 (1996).
23. Campagnari, A. A., et al., *Infection and Immunity*, 62, 4909–4914 (1994).
24. Campagnari, A. A., et al., *Infection and Immun.*, 64, 3920–3924 (1996).
25. Ferreiros, C. M., et al., *EMS Micro. Letters*, 83, 247–254 (1991).
26. Danve, B., et al., *Vaccine*, 11, 1214–1220 (1993).
27. Maciver, I., et al., *J. Infect. Dis.*, 168, 469–72 (1993).
28. Lissolo, L., et al., *Infection and Immunity*, 63, 884–890 (1995).
29. Gerlach, G. F., et al., *Infection and Immunity*, 60, 3253–3261 (1992).
30. Gray-Owen, S. D., and Schryvers, A. B., *Trends in Microbiol.*, 4, 185–191 (1996).
31. Tsunasawa, S., and Hirano, H., in "Methods in Protein Sequence Analysis", pages 45–53 (K. Imahori and F. Sakiyama, Eds.), Plenum Press, New York, New York (1993).
32. Unhanand, M., et al., *J. Infect. Dis.*, 165, 644–650 (1992).
33. Verghese, A., et al., *J. Infect. Dis.*, 162, 1189–1192 (1990).
34. Laemmli, U. K., *Nature*, 227, 680–685 (1970).
35. Hillenkamp, F., and Karas, M., *Methods Enzymol.*, 193, 280–295 (1990).
36. Arrizon-Lopez, V., et al., in "High-Performance Liquid Chromatography of Peptides and Proteins: Separation, Analysis and Conformation", pages 859–863 (C. T. Mant and R. S. Hodges, Eds.), CRC Press, Boca Raton, Fla. (1991).
37. Matsudaira, P., *J. Biol. Chem.*, 262, 10035–10038 (1987).
38. Sengoku, Y., et al., in "Protein Analysis Renaissance", pages 25–28, Applied Biosystems, Foster City, Calif. (1993).
39. Bhown, A. S., et al., *Anal. Biochem.*, 131, 337–340 (1983).
40. Aitken, A., in "Laboratory Methodology in Biochemistry. Amino Acid Analysis and Protein Sequencing", page 26 (C. Fini, et al., Eds.), CRC Press, Boca Raton, Fla. (1990).
41. Schägger, H., and von Jagow, G., *Anal. Biochem.*, 166, 368–379 (1987).

What is claimed is:

1. A method of immunizing a human host against *M. catarrhalis* which comprises administering to said host an immunogenic amount of a vaccine composition comprising an isolated and purified 74 kD protein of *M. catarrhalis*, wherein the 74 kD protein has:
   (a) a molecular weight of 74 kD as measured by mass spectrometry;
   (b) the amo-terinal amino acid sequence of Xaa Gly Gly Ser Gly Gly Ser Asn Pro Pro Ala Pro Thr (SEQ ID No:1), where the first residue is not identified; and
   (c) the protein has an amino acid composition of about 104 Asp+Asn residues/mole, 58 Thr residues/mole, 44 Ser residues/mole, 67 Glu+Gln residues/mole, 27 Pro residues/mole, 77 Gly residues/mole, 56 Ala residues/mole, 35 Val residues/mole, 6 Met residues/mole, 21 Ile residues/mole, 40 Leu residues/mole, 25 Tyr residues/mole, 28 Phe residues/mole, 8 His residues/mole, 72 Lys residues/mole and 21 Arg residues/mole,
   wherein the composition elicits a protective immune response.

2. The method of claim 1 wherein the isolated and purified 74 kD protein has the amino-terminal amino acid sequence: Xaa Gly Gly Ser Gly Gly Ser Asn Pro Pro Ala Pro Ihr Pro Ile Pro Asn (SEQ ID NO:2).

3. The method of claim 1 wherein the isolated and purified 74 kD protein has the amino-terminal amino acid sequence; Xaa Gly Gly Ser Gly Gly Ser Asn Pro Pro Ala Pro Thr Pro Ile Pro Asn Ala (SEQ ID NO:5).

4. The method of claim 1 wherein the isolated and purified 74 kD protein has the amino-terminal amino acid sequence: Xaa Gly Gly Ser Gly Gly Ser Asn Pro Pro Ala Pro Thr Pro Ile Pro Asn Ala Ser Gly (SEQ ID NO:3).

5. The method of claim 1 wherein the isolated and purified 74 kD protein has the amino-terminal amino acid sequence: Xaa Gly Gly Ser Gly Gly Ser Asn Pro Pro Ala Pro Thr Pro Ile Pro Asn Ala Ser Gly Ser Gly Asn Thr Gly Asn Thr (SEQ ID NO:4).

6. The method of claim 1 which further comprises administering to a human host at least one additional *M. catarrhalis* antigen.

7. The method of claim 6 wherein the additional *M. catarrhalis* antigen is selected from the group consisting of the proteins designated CopB, UspA, OMP C/D and OMPE.

8. The method of claim 1 wherein the 74 kD protein is coupled to an agent which protects against another pathogenic organism.

9. The method of claim 1 wherein the 74 kD protein is coupled to another antigenic moiety of *M. catarrhalis*.

10. The method of claim 1 wherein the 74 kD protein is isolated and purified from TTA24 strain.

* * * * *